US011172993B2

(12) United States Patent
Bai et al.

(10) Patent No.: US 11,172,993 B2
(45) Date of Patent: Nov. 16, 2021

(54) SENSORED SURGICAL TOOL AND SURGICAL INTRAOPERATIVE TRACKING AND IMAGING SYSTEM INCORPORATING SAME

(71) Applicant: SYNAPTIVE MEDICAL INC., Toronto (CA)

(72) Inventors: Yanhui Bai, Toronto (CA); Michael Frank Gunter Wood, Toronto (CA); Cameron Anthony Piron, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 525 days.

(21) Appl. No.: 15/896,516

(22) Filed: Feb. 14, 2018

(65) Prior Publication Data
US 2018/0228553 A1 Aug. 16, 2018

(30) Foreign Application Priority Data

Feb. 15, 2017 (CA) .................................. CA 2957977

(51) Int. Cl.
*A61B 34/20* (2016.01)
*A61B 90/00* (2016.01)
(Continued)

(52) U.S. Cl.
CPC .............. *A61B 34/20* (2016.02); *A61B 34/30* (2016.02); *A61B 90/361* (2016.02); *A61B 17/34* (2013.01);
(Continued)

(58) Field of Classification Search
CPC .......... A61B 34/2068; A61B 2090/367; A61B 2090/3983; A61B 17/34; A61B 1/00193
See application file for complete search history.

(56) References Cited

U.S. PATENT DOCUMENTS 5,305,121 A * 4/1994 Moll ........................ A61B 1/05
348/45
6,149,581 A * 11/2000 Klingenstein ............ A61B 1/31
600/114
(Continued)

FOREIGN PATENT DOCUMENTS

WO 2010146587 A1 12/2010
WO 2014004717 A2 1/2014
(Continued)

OTHER PUBLICATIONS

Ge Y., Wang M., Chen X., Ron H., An optical MEMS pressure sensor based on a phase demodulation method, Sensors and Actuators A: Physical, vol. 143, Nov. 17, 2007, pp. 224-229.
(Continued)

*Primary Examiner* — Alexandra L Newton
*Assistant Examiner* — Jae Woo

(57) ABSTRACT

Described are various embodiments of a sensored surgical tool, and surgical intraoperative tracking and imaging system incorporating same. In one embodiment, the surgical tool comprises a rigid elongate tool body having a substantially rigid tool tip to be displaced and tracked within the surgical cavity so to reproducibly locate the tool tip within the cavity. The tool further comprises one or more tool tip cameras and/or pressure sensors operatively disposed along the body at or proximal to the tool tip.

20 Claims, 12 Drawing Sheets

(51) Int. Cl.
*A61B 34/30* (2016.01)
*A61B 17/34* (2006.01)

(52) U.S. Cl.
CPC ............ *A61B 2034/2051* (2016.02); *A61B 2034/2055* (2016.02); *A61B 2034/2068* (2016.02); *A61B 2090/064* (2016.02); *A61B 2090/065* (2016.02); *A61B 2090/367* (2016.02); *A61B 2090/3983* (2016.02); *A61B 2218/007* (2013.01)

(56) References Cited

U.S. PATENT DOCUMENTS

| | | | | |
|---|---|---|---|---|
| 8,611,983 | B2* | 12/2013 | Glossop | A61B 1/2676 600/414 |
| 2002/0007110 | A1* | 1/2002 | Irion | A61B 1/05 600/170 |
| 2004/0034311 | A1* | 2/2004 | Mihalcik | A61B 1/00165 600/585 |
| 2004/0220478 | A1* | 11/2004 | Wallace | A61B 1/00096 600/476 |
| 2006/0184016 | A1* | 8/2006 | Glossop | A61B 1/2676 600/434 |
| 2007/0225634 | A1* | 9/2007 | Ferren | A61B 17/12022 604/27 |
| 2007/0299351 | A1* | 12/2007 | Harlev | A61B 5/0245 600/509 |
| 2008/0208006 | A1* | 8/2008 | Farr | A61B 1/0684 600/178 |
| 2009/0187069 | A1* | 7/2009 | Terliuc | A61B 1/0055 600/106 |
| 2009/0221908 | A1* | 9/2009 | Glossop | A61B 17/3403 600/424 |
| 2009/0318758 | A1* | 12/2009 | Farr | A61B 90/53 600/112 |
| 2010/0198009 | A1* | 8/2010 | Farr | A61B 90/53 600/109 |
| 2011/0015649 | A1* | 1/2011 | Anvari | A61B 34/20 606/130 |
| 2011/0301414 | A1* | 12/2011 | Hotto | A61B 1/00055 600/114 |
| 2012/0143029 | A1* | 6/2012 | Silverstein | A61B 5/7475 600/374 |
| 2013/0204097 | A1* | 8/2013 | Rondoni | A61B 5/4893 600/301 |
| 2014/0272773 | A1* | 9/2014 | Merritt | A61B 6/145 433/29 |
| 2014/0276007 | A1 | 9/2014 | Sela et al. | |
| 2015/0037775 | A1* | 2/2015 | Ottensmeyer | G09B 23/30 434/271 |
| 2015/0173673 | A1 | 6/2015 | Toth et al. | |
| 2015/0182191 | A1* | 7/2015 | Caluser | A61B 5/061 600/440 |
| 2016/0008074 | A1* | 1/2016 | Glossop | A61B 17/0218 606/130 |
| 2017/0020623 | A1* | 1/2017 | Glossop | A61B 34/10 |
| 2017/0151022 | A1* | 6/2017 | Jascob | A61B 90/39 |
| 2017/0188793 | A1* | 7/2017 | Ouyang | A61B 1/00103 |
| 2017/0245940 | A1* | 8/2017 | Piron | G06T 7/0014 |
| 2018/0132700 | A1* | 5/2018 | Ouyang | A61B 1/00135 |

FOREIGN PATENT DOCUMENTS

| | | |
|---|---|---|
| WO | 2016041046 A1 | 3/2016 |
| WO | 2016107615 A1 | 7/2016 |
| WO | 2016160463 A1 | 10/2016 |
| WO | 2016161496 A1 | 10/2016 |

OTHER PUBLICATIONS

Hill G.C., Melamud R., Declercq F.E., Davenport A.A., Chan I.H., Hartwell P.G., Pruitt B.L., SU-8 MEMS Fabry-Perot pressure sensor, Sensors and Actuators A: Physical 138, Apr. 22, 2007, pp. 52-62.

Manjila S., Mencattelli M., Rosa B., Price K., Fagogenis G., Dupont P. E., A multiport MR-compatible neuro endoscope: spanning the gap between rigid and flexible scopes, Neurosurgical Focus 41 (3): E13, 2016, pp. 1-15.

NanEye Camera System Spec, Awaiba, Version 1.0.14, Aug. 17, 2012, pp. 1-10.

Yao J.L., Yang X., Shao N., Luo H., Zhang T., Jiang W.G., A Flexible and Highly Sensitive Piezoresistive Pressure Sensor Based on Micropatterned Films Coated with Carbon Nanotubes, Journal of Nanomaterials, vol. 2016, Jul. 12, 2016, pp. 1-6.

* cited by examiner

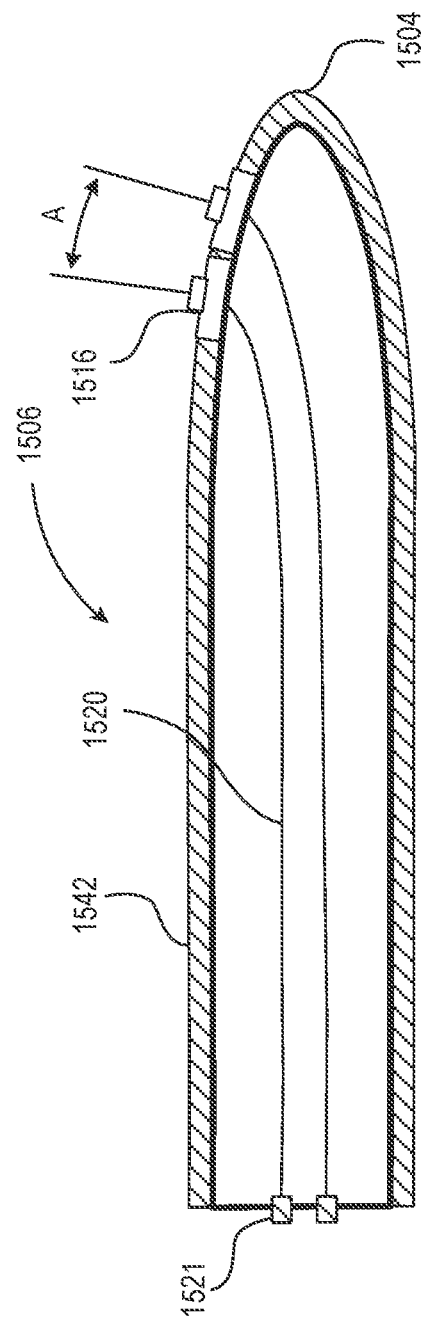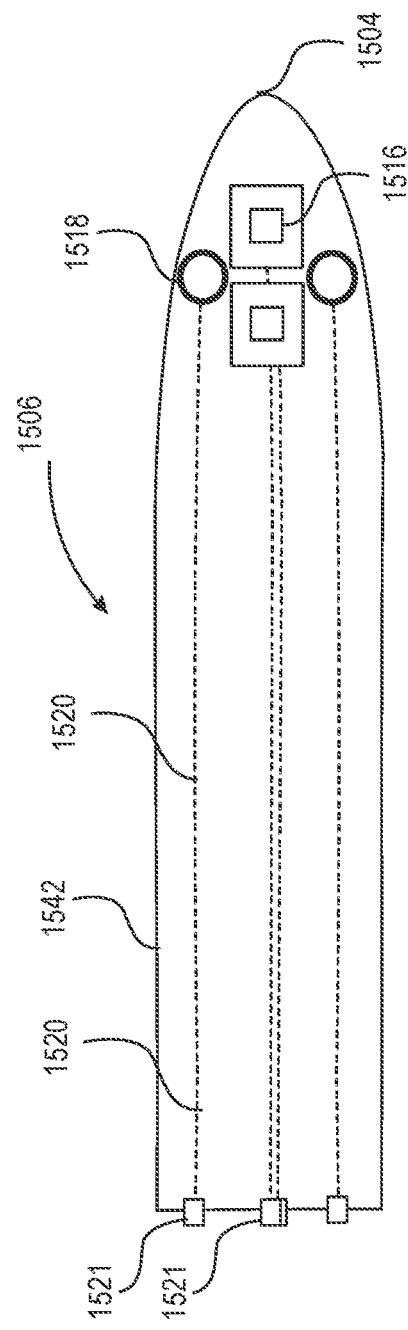

SENSORED SURGICAL TOOL AND SURGICAL INTRAOPERATIVE TRACKING AND IMAGING SYSTEM INCORPORATING SAME

CROSS REFERENCE TO RELATED APPLICATIONS

This application claims the benefit of Canadian Patent Application No. 2,957,977, filed Feb. 15, 2017, which is incorporated herein by reference in its entirety.

FIELD OF THE DISCLOSURE

The present disclosure relates to surgical instruments, tools and systems, and, in particular, to a sensored surgical tool for use, for example, within a surgical cavity, such as an open port-based or visually accessible surgical cavity, and a surgical system incorporating such tool, such as a surgical intraoperative tracking and imaging system.

BACKGROUND

Various surgical site imaging techniques and tools have been developed to improve the accuracy and ultimate success of a given surgical procedure. Known imaging tools for visually closed-access surgical procedures, for example those channeled through an anatomical lumen (e.g., vascular, intestinal procedures), may include fiber optic scopes, optical coherence tomography (OCT) probes, micro ultrasound transducers and the like, wherein a generally flexible tool is inserted and channeled to a surgical site of interest.

Visually open-access surgical sites, for example, those employing a surgical access port or the like, generally rely on external imaging devices, such as an overhead down-cavity surgical microscope or an external videoscope and display system. Accordingly, surgical site imaging is generally limited to the different fields of view and view angles available to the external scope and/or surgical microscope which not only generally limits visibility to down-port images, but is also subject to visibility issues when blood or other fluids immerse the surgical cavity or port bottom. Given the limited working space within the port/cavity, and, particularly, for neurosurgical applications, the highly critical nature of any down-port maneuvers and/or tissue interactions, limited visibility can result in significant surgical challenges, particularly, for example, when seeking to blindly locate and address a bleeding site or evaluate externally visually inaccessible areas within the cavity, such as areas blocked by visually interfering tissue.

Currently, a surgeon will generally seek to reduce the volume of visually interfering fluids using a suction tool in an attempt to identify and address a bleeding/leaking site, for example, before the cavity/port is re-immersed with fluid. As for gaining visibility around or below visually interfering tissue, the surgeon may rather seek to re-angle the external scope or microscope, albeit within field of view and view angle limits prescribed by the external equipment and surgical cavity/port. Accordingly, significant challenges remain in adequately visualizing, characterizing and addressing visually inaccessible, obscured or obstructed portions of the surgical cavity.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a sensored surgical tool, and surgical system incorporating same, that overcome some of the drawbacks of known techniques, or at least, provides a useful alternative thereto. Some aspects of this disclosure provide examples of such tools and systems.

For instance, in accordance with some aspects of the present disclosure, a sensored surgical tool is described for use in a surgical cavity to provide increased intraoperative inner-cavity visibility and characterization to supplement external imaging device capabilities, for example, to access, image and/or characterize obscured, obstructed or otherwise externally visually inaccessible regions of the surgical cavity. In some aspects, such enhanced inner-cavity characterization may improve intraoperative imaging of the cavity while also assisting in locating and addressing inner-cavity bleeding or other fluid immersions, for example, by location-tracking and mapping imaging and characterization capabilities of the herein-described tools and systems.

In accordance with one aspect, there is provided a surgical tool for use within a surgical cavity, the surgical tool comprising: a rigid elongate tool body having a substantially rigid tool tip to be displaced and tracked within the surgical cavity so to reproducibly locate said tool tip within the cavity; and a pressure sensor operatively disposed along said body at or proximal to said tool tip and responsive to pressure variations applied thereto from within the surgical cavity to output a sensor signal representative thereof as the tool is displaced within the cavity, wherein said sensor signal is externally communicable to associate respective inner-cavity pressure readings with tracked tool tip locations.

In one embodiment, the pressure sensor is laterally oriented relative to said tip.

In one embodiment, the surgical tool further comprises two or more said pressure sensor at or proximate said tool tip.

In one embodiment, the surgical tool further comprises a set of fiducial markers externally coupled in a fixed configuration to an externally extending portion of said elongate body, wherein said markers are trackable by an external tracking system to automatically determine said tracked tool tip locations with reference to the cavity based on a respective tracked position of said markers.

In one embodiment, the surgical tool further comprises a radio frequency transmitter to wirelessly communicate said sensor signal.

In one embodiment, the pressure sensor comprises two or more pressure sensors collocated at or toward said tool tip.

In one embodiment, the surgical tool further comprises a suction tool at or proximal to said tip to concurrently provide suction within the surgical cavity around said tip.

In one embodiment, the surgical cavity is externally visible to an external camera aligned therewith, and wherein said tip is operable as a trackable pointer within the cavity.
}

In one embodiment, the surgical tool further comprises at least one camera disposed and laterally-oriented along said body at or proximal to said tip so to capture lateral images from within the surgical cavity, wherein said lateral images are externally communicable to associate respective inner-cavity images with tracked tool tip locations.

In one embodiment, the surgical tool further comprises at least one complementary camera disposed along said body at or proximal to said tip so to capture complementary images of the surgical cavity along a complementary imaging axis angled downwardly relative to said laterally-oriented camera so to construct a 3D inner-cavity mapping or an enlarged field of view image of the surgical cavity from said lateral images and said complementary images.

In one embodiment, the surgical cavity is visibly accessible to an external camera or scope aligned therewith, and wherein said inner-cavity images are complementary to external images captured by said external camera or scope in enhancing inner-cavity visualization.

In one embodiment, the tip is movable within the cavity to track pressure variations resulting from inner-cavity bleeding in locating a bleeding site within the cavity.

In one embodiment, the tool body comprises a reusable tool shaft portion and a disposable tool tip portion removably operatively connectable to said shaft portion, wherein said tip portion comprises said tip and said pressure sensor.

In accordance with another aspect, there is provided a surgical system for performing surgery through an externally accessible surgical cavity, the system comprising: a surgical tool comprising: a rigid elongate tool body having a substantially rigid tool tip to be displaced and tracked within the surgical cavity so to reproducibly locate said tool tip within the cavity; and a pressure sensor operatively disposed along said body at or proximal to said tool tip and responsive to pressure variations applied thereto from within the surgical cavity to output a sensor signal representative thereof as the tool is displaced within the cavity; an external tracking system operatively interfacing with said surgical tool to automatically track a location of said tool tip within the cavity; and an external data processing unit operable to associate a given pressure reading associated with said sensor signal with a corresponding location of said pressure sensor within the cavity.

In one embodiment, the system further comprises a set of fiducial markers externally coupled in a fixed configuration to an externally extending portion of said elongate body, and wherein said markers are trackable by an external surgical navigation system to automatically associate said corresponding location of said pressure sensor within the cavity based on a respectively tracked position of said markers.

In one embodiment, the pressure sensor is laterally oriented relative to said tip.

In accordance with another aspect, there is provided a surgical tool for use within a surgical cavity, the surgical tool comprising: a rigid elongate tool body having a substantially rigid tool tip to be displaced and tracked within the surgical cavity so to reproducibly locate said tool tip within the cavity; and at least one laterally-oriented camera operatively disposed along said body at or proximal to said tip so to capture lateral inner-cavity images of the surgical cavity for output as the tool is displaced within the cavity, wherein said lateral inner-cavity images are externally communicable to associate respective lateral inner-cavity images with tracked tool tip locations.

In one embodiment, the surgical tool further comprises a set of fiducial markers externally coupled in a fixed configuration to an externally extending portion of said elongate body, wherein said markers are trackable by an external tracking system to automatically determine said tracked tool tip locations with reference to the cavity based on a respective tracked position of said markers.

In one embodiment, the surgical tool further comprises a radio frequency transmitter to wirelessly communicate said lateral inner-cavity images.

In one embodiment, the surgical tool further comprises a suction tool at or proximal to said tip to concurrently provide suction within the surgical cavity around said tip.

In one embodiment, the surgical tool further comprises at least one complementary camera disposed along said body at or proximal to said tip so to capture complementary images of the surgical cavity along a complementary imaging axis angled downwardly relative to said laterally-oriented camera so to construct a 3D inner-cavity mapping or an enlarged field of view image of the surgical cavity from said lateral images and said complementary images.

In one embodiment, the surgical cavity is visibly accessible to an external camera or scope aligned therewith, and said inner-cavity images are complementary to external images captured by said external camera or scope in enhancing inner-cavity visualization.

In one embodiment, the tool body comprises a reusable tool shaft portion and a disposable tool tip portion removably operatively connectable to said shaft portion, wherein said tip portion comprises said tip and said camera.

In accordance with another aspect, there is provided a surgical system for performing surgical procedures via a surgical cavity, the system comprising: a surgical tool comprising: a rigid elongate tool body having a substantially rigid tool tip to be displaced and tracked within the surgical cavity so to reproducibly locate said tool tip within the cavity; and at least one laterally-oriented camera operatively disposed along said body at or proximal to said tip so to capture lateral inner-cavity images of the surgical cavity for output as the tool is displaced within the cavity, wherein said lateral inner-cavity images are externally communicable to associate respective lateral inner-cavity images with tracked tool tip locations; an external tracking system operatively interfacing with said surgical tool to automatically track a location of said tool tip within the cavity; and an external image processing unit operable to associate a given lateral inner-cavity image captured via said camera with a corresponding location of said camera within the cavity.

In one embodiment, the system further comprises an external imaging device axially aligned with the surgical cavity to capture downward images thereof; wherein said image processing unit is further operable to concurrently render downward images and lateral images of the surgical cavity as the surgical tool is moved.

In one embodiment, the camera has a footprint no greater than about 2 mm×2 mm, or no greater than about 1 mm×1 mm.

In one embodiment, the camera operates in a spectral region selected from visible and a near infrared.

In one embodiment, the surgical cavity is at least partially defined by a surgical port.

In one embodiment, the system further comprises a set of fiducial markers externally coupled in a fixed configuration to an externally extending portion of said elongate body; wherein said markers are trackable by said external tracking system to automatically determine said tracked tool tip locations with reference to the cavity based on a respective tracked position of said markers.

In one embodiment, the image processing unit is further operable to map an internal region of the surgical cavity by digitally assembling a set of said lateral images corresponding to said region and mapped thereto via each said corresponding location.

In one embodiment, the tool further comprises at least one complementary camera disposed along said body at or proximal to said tip so to capture complementary images of the surgical cavity along a complementary imaging axis angled downwardly relative to said laterally-oriented camera so to construct a 3D inner-cavity mapping or an enlarged field of view image of the surgical cavity from said lateral images and said complementary images.

Other aspects, features and/or advantages will become more apparent upon reading the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 4A is a schematic cross-sectional view of a disposable tool tip portion of the sensored surgical tool of FIG. 3, in accordance with an embodiment of the present disclosure;

FIG. 4B is a schematic top plan view of the disposable tool tip portion shown in FIG. 4A;

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiment are often not depicted in order to facilitate a less obstructed view of these various embodiments of the present disclosure.

DETAILED DESCRIPTION

The embodiments described herein provide different examples of a sensored to surgical tool, and system incorporating same. The tools, systems and methods described herein may be useful in the field neurosurgery, including oncological care, neurodegenerative disease, stroke, brain trauma, and orthopedic surgery. However, the subject matter of the present disclosure may extend or apply to other conditions or fields of medicine, and such extensions or applications are encompassed by the present disclosure. For example, the tools, systems and methods described herein encompass surgical processes that are applicable to surgical procedures for brain, spine, knee, and any other region of the body that will benefit from the use of an access port or small open orifice to define and access a surgical cavity within the interior of an animal body, such as a human body.

Various tools, systems, apparatuses, devices, or processes are below-described and provide examples of sensored surgical tools, and systems incorporating same, in accordance with embodiments of the present disclosure. None of the below-described embodiments limits any claimed embodiment; and any claimed embodiment may also encompass tools, systems, apparatuses, devices, or processes that may differ from the below-described examples. The claimed embodiments are not limited to tools, systems, apparatuses, devices, or processes having all of the features of any one of the below-described tools, systems, apparatuses, devices, or processes or to features common to some or all of the below-described tools, systems, apparatus, devices, or processes.

Furthermore, this Detailed Description sets forth numerous specific details in order to provide a thorough understanding of the various embodiments described throughout the present disclosure. However, it will be understood by those of ordinary skill in the art that the embodiments described herein may be practiced without these specific details. In other instances, well-known methods, procedures and components have not been described in detail so as not to obscure the embodiments described herein.

Figure 1:
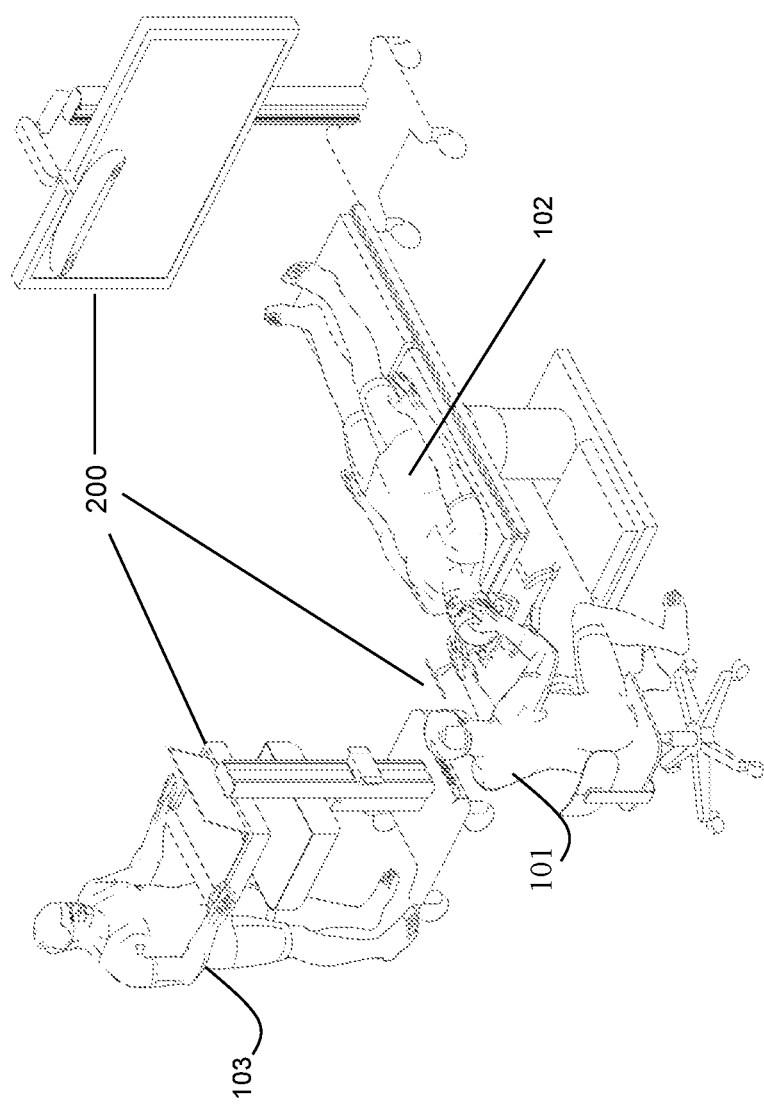
FIG. 1 is a diagram illustrating a perspective view of a navigation system, such as a medical navigation system, comprising a patient reference device, in an environmental context, such as an operation room, in accordance with an embodiment of the present disclosure.
Figure 2:
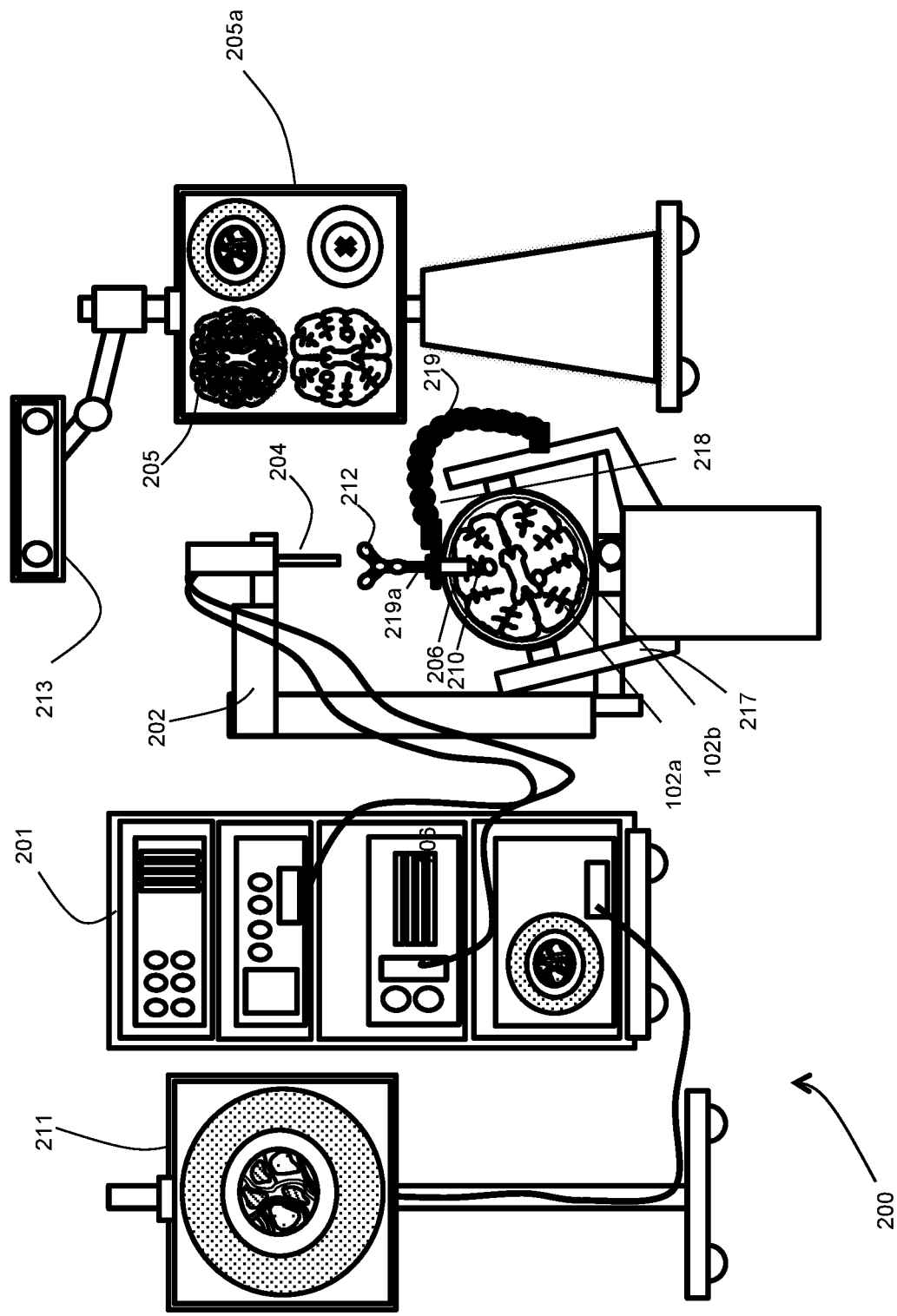
FIG. 2 is a schematic diagram illustrating a navigation system, such as a medical navigation system, comprising a patient reference device, in accordance with an embodiment of the present disclosure.

With reference to FIGS. 1 and 2, and in accordance with one embodiment, an exemplary port-based surgical system incorporating a sensored surgical tool, will now be described. As noted above, it will be appreciated that the sensored surgical tool described herein within the context of a port-based surgical system and associated tracking/navigation system, may also be amenable to other similar or alternate surgical systems and procedures, and that, without departing from the general scope and nature of the present disclosure. Namely, the utility and applicability of the herein-described sensored surgical tool is not limited to port-based and/or neurological procedures, but rather, may prove particularly useful and desirable in a number of surgical environments in which one or more tracked surgical tools are to be operated within a given surgical cavity where inner-cavity imaging and/or characterization is otherwise obscured or hidden from the surgeon or other medical practitioner.

In the illustrated examples, the surgical system encompasses an exemplary surgical navigation system 200 operable to track various patient reference devices, in an environmental context, such as an operation room (OR). The system 200 supports, facilitates, and enhances minimally invasive access port-based surgery using a minimally invasive access port-based surgical procedure, though non port-based procedures may equally be considered herein as noted above.

By example only, a surgeon 101 conducts a minimally invasive access port based surgery on a subject, such as a patient 102, in an OR environment. The navigation system 200 generally includes an equipment tower 201, a robotic arm 202 to support an external optical scope 204, and at least one display or monitor 205, 211 for displaying a video image. By example only, an operator 103 is also present to operate, control, and provide assistance for the system 200.

With particular reference to FIG. 2, the equipment tower 201 is generally mountable on a frame, e.g., a rack or a cart, and is configured to accommodate a power supply, e.g., an AC adapter power supply, and at least one computer or controller operable by at least one a set of instructions, storable in relation to at least one non-transitory memory device, corresponding to at least one of surgical planning software, navigation/tracking software, or robotic software for managing at least one of the robotic arm 202 and at least one instrument, such as a surgical instrument, e.g., the access port 206, the introducer 210, and/or one or more other downstream (instrumented) surgical tools (not shown) used during the procedure. For example, the computer comprises at least one of a control unit and a processing unit, such as control and processing unit 400 or 1530 schematically shown in FIGS. 8 and 3, respectively. In the illustrated embodiment, the equipment tower 201 comprises a single tower configured to facilitate coupling of the at least one display device. e.g., a primary display device 211 and a secondary display device 205, with the at least one piece of equipment. However, other configurations are also encompassed by the present disclosure, such as the equipment tower 201 comprising dual towers configured to facilitate coupling of a single display, etc. The equipment tower 201 is also configurable to accommodate an uninterruptible power supply (UPS) for providing emergency power.

To maintain constant positioning of the patient's anatomy of interest during a given procedure, the patient's anatomy may be held in place by a holder appropriate for the procedure in question. For example, in a port-based neurosurgical procedure, such as that illustrated in FIG. 2, a patient's head can be retained by a head holder 217. A craniotomy is performed; and a dura flap is formed and retracted. The access port 206 and introducer 210 can then be inserted into the patient's brain 102b; and the planned procedure is executed while the patient's head remains effectively immobile.

The system also includes a tracking system 213 that is generally configured to track at least one instrument, such as a surgical instrument or tool. In FIGS. 1 and 2, the tracking system is initially utilized to track the access port 206 and introducer 210 while the access port is being introduced within the patient's brain so to ultimately locate and define the surgical site and surrounding surgical cavity. However, other sensored or non-sensored intra-operative surgical tools, such as, but not limited to, inner-cavity pointing tools, suction tools, tissue probes (e.g. Raman, OCT probes, etc.), resection tools and the like, are also advantageously tracked by the tracking system to enhance accuracy and precision of executed operative procedures. Instrument tracking can thus significantly assist the surgeon 101 during the minimally invasive access port-based surgical procedure (or like procedures) both in guiding and confirming procedural actions, but also in aligning real-time surgical cavity imaging and characterization, as detailed below within the context of tip-sensored surgical tools, with pre-operative imaging data and intra-operative external imaging (e.g. captured via external optical scope 204 and/or other cameras discussed below). Accordingly, tracking sensored tools such as pointing and/or suction tools can significantly benefit enhanced or complementary inner-cavity imaging, localization, characterization and/or mapping.

Accordingly, the tracking system 213 is configured to track and determine, e.g., in real-time by way of a set of instructions corresponding to tracking software and storable in relation to at least one non-transitory memory device, the location of the one or more tracked instruments during the surgical procedure, while also generally tracking a position of the robotic arm 202.

In the illustrated embodiment, the tracking system 213 generally comprises at least one sensor (not shown) for detecting at least one fiducial marker 212 disposable in relation the one or more OR items (e.g. surgical arm 202) and/or surgical instruments (introducer 210) to be tracked. In one example, the tracking system 213 comprises a three-dimensional (3D) optical tracking stereo camera, such as a Northern Digital Imaging® (NDI) optical tracking stereo camera, which can be configured to locate reflective sphere tracking markers 212 in 3D space. In another example, the tracking camera 213 may be a magnetic camera, such as a field transmitter, where receiver coils are used to locate objects in 3D space, as is also known in the art. Accordingly, location data of the mechanical arm 202, access port 206, introducer 210 and its associated pointing tool, and/or other tracked instruments/tools, may be determined by the tracking camera 213 by automated detection of tracking markers 212 placed on these tools, wherein the 3D position and orientation of these tools can be effectively inferred and tracked by tracking software from the respective position of the tracked markers 212.

In the illustrated embodiment of FIG. 2, the secondary display 205 provides an output of the tracking camera 213, which may include, but is not limited to, axial, sagittal and/or coronal views as part of a multi-view display, for example, and/or other views as may be appropriate, such as views oriented relative to the at least one tracked instrument (e.g. perpendicular to a tool tip, in-plane of a tool shaft, etc.). These and other views may be considered in various single or multi-view combinations, without departing from the general scope and nature of the present disclosure.

Still referring to FIG. 2, minimally invasive brain surgery using access ports is a recent method of performing surgery on brain tumors. In order to introduce an access port 206 into a brain, such as the patient's brain 102b, of a patient head's 102a, an introducer, e.g., the introducer 210, comprises an atraumatic tip disposable within the access port 206 to facilitate positioning the access port 206 within the patient brain 102b. As noted above, the introducer 210 further comprises at least one fiducial marker 212 for facilitating tracking by the tracking system 213. Generally, tracked tools such as introducer 210 will include a plurality of fiducial markers to enhance trackability in 3D space.

After the introducer 210 and the access port 206 are inserted into the brain 102*b*, the introducer 210 is removed to facilitate access to the tissue of the brain 102*b* through the central opening of the access port 206. However, after the introducer 210 is removed, the access port 206 is no longer being tracked by the tracking system 213. However, the access port 206 is indirectly trackable by way of additional pointing tools (not shown) configured for identification by the navigation system 200.

In the illustrated embodiment of FIG. 2, the navigation system 200 further comprises a guide clamp 218 for retaining the access port 206. The guide clamp 218 is configured to optionally engage and disengage the access port 206, eliminating the need to remove the access port 206 from the patient 102. In some embodiments, the access port 206 is configured to slide up and down within the guide clamp 218 in a closed position. The guide clamp 218 further comprises a locking mechanism (not shown), the locking mechanism being attachable or integrable in relation to the guide clamp 218, and the locking mechanism being optionally manually actuatable, e.g., using one hand as further below described.

The navigation system 200 further comprises an articulating arm 219, such as a small articulating arm, configured to couple with the guide clamp 218. The articulating arm 219 comprises up to six (6) degrees of freedom for facilitating positioning of the guide clamp 218. The articulating arm 219 is attachable at a location in relation to the head holder 217, or in relation to any other suitable patient support structure, to ensure, when locked in place, that the guide clamp 218 is fixed in relation to the patient's head 102*a*. The articulating arm 219 comprises an interface 219*a* disposable in relation to the guide clamp 218, wherein the interface 219*a* is at least one of flexible or lockable into place. Flexibility of the interface 219*a* facilitates movability of the access port 206 into various positions within the brain 102*b*, yet still maintains rotatability about a fixed point.

The navigation system 200 may further or alternatively comprise a plurality of wide-field cameras, e.g., two additional wide-field cameras (not shown) being implemented with video overlay information, wherein one camera is mountable in relation to the optical scope 204 and the other camera is mountable in relation to the navigation system 213 (i.e. within the context of an electromagnetic tracking system). In the case of the navigation system 213 comprising an optical tracking device, a video image can be directly extracted therefrom. Video overlay information can then be used to enhance available intra-operative information, for example, by providing an image displaying a physical space and confirming tracking system registration alignment and optional corresponding text and/or indicia, an image displaying a motion range of the robotic arm 202 holding the optical scope 204 and optional corresponding text and/or indicia, and/or an image displaying a guide head positioning and a patient positioning and optional corresponding text and/or indicia.

Figure 3:
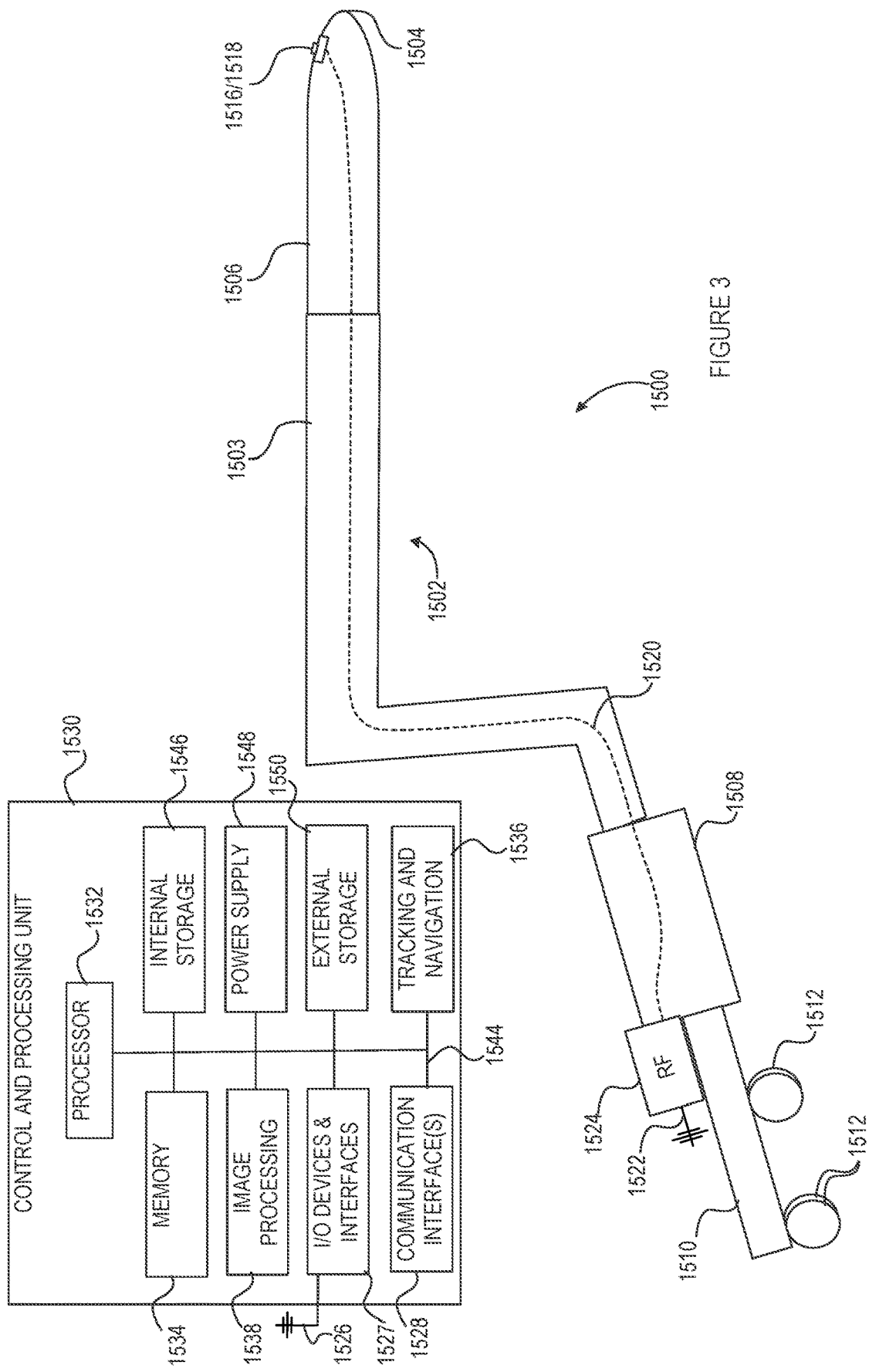
FIG. 3 is a schematic diagram of a sensored surgical tool and associated control and processing unit, in accordance with an embodiment of the present disclosure.

Other image overlays, as will be described in greater detail below, may further include intraoperative cavity imaging and/or characterization data (e.g. colour mapping, partial image transparency overlay, text and/or indicia), such as provided by a sensed tool, (i.e. as shown in FIGS. 3, 4A and 4B), for example including, but not limited to, real-time inner cavity images (e.g. visible, near infrared (IR), etc.) provided by tool tip mounted camera(s), real-time inner cavity pressure readings (e.g. localized fluid pressure readings, pressure gradients, pressure mappings, etc.) provided by tool tip mounted pressure sensor(s) and/or sensor arrays, and other such readings of interest given the application at hand. Using such real-time intraoperative inner cavity imaging and characterization data may not only enhance other intraoperative images, such as those rendered by overhead scopes and/or cameras, but also seamlessly integrate with pre-operative images and/or data, for instance, acquired pre-operatively using one more imaging techniques. Accordingly, the surgeon and/or other surgical equipment operator can execute procedures and/or actions with greater clarity, certainty and visibility, thus leading to improved outcomes and risk reduction.

Figure 5:
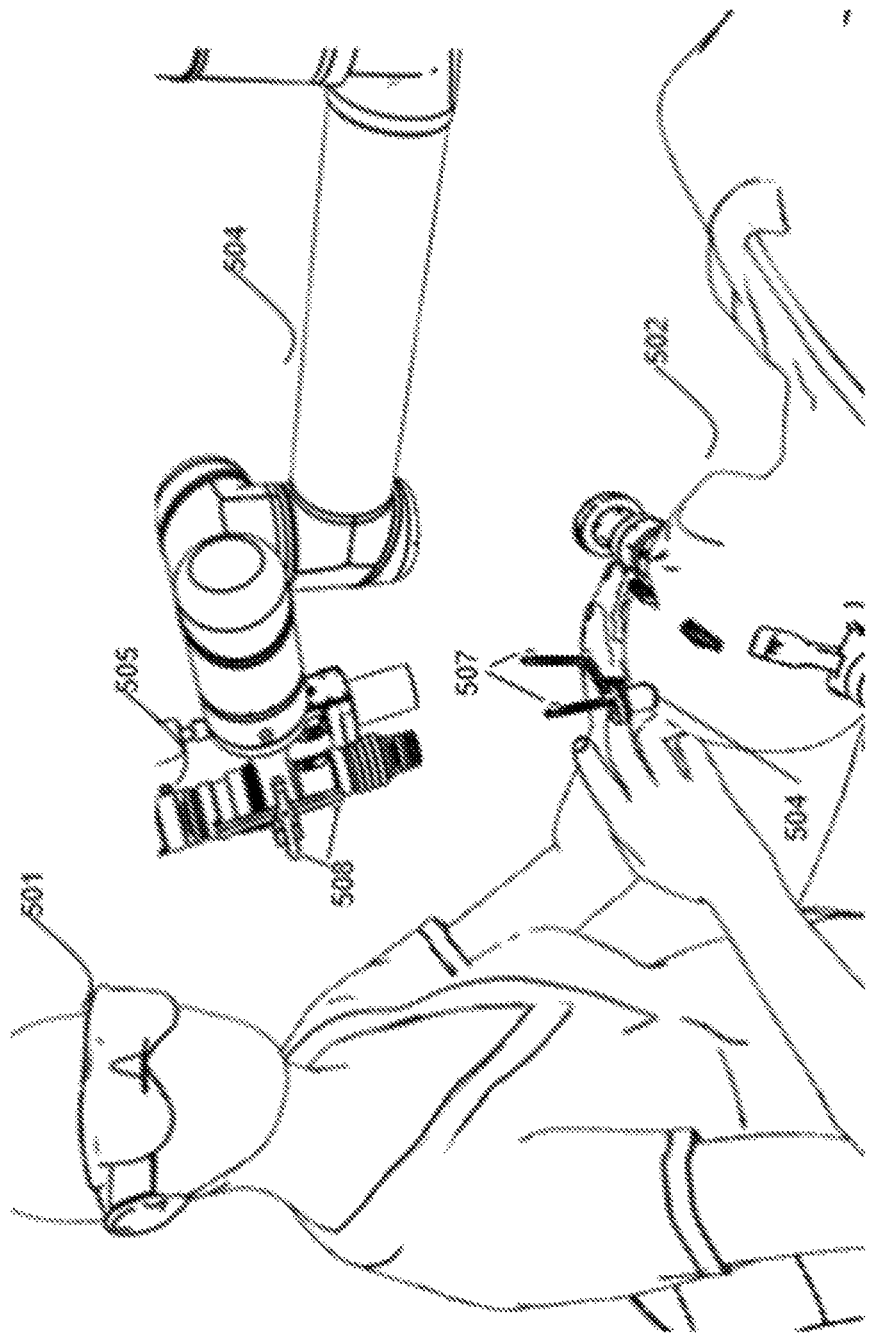
FIG. 5 is a diagram illustrating an access port-based surgical procedure being conducted by way of a navigation system, in accordance with some embodiments of the present disclosure.

With reference to FIG. 5, a diagram of an access port-based surgical procedure conducted by way of the navigation system 200 is illustrated, in accordance with some embodiments of the present disclosure. In this example, a surgeon 501 is resecting a tumor from the brain of a patient 502 through an access port 504. An external scope 505 is coupled with a robotic arm 504, and is used to view down port 504 at a sufficient magnification to allow for enhanced visibility down port 504. The output of external scope 505 is rendered on a visual display.

As introduced above, the procedure illustrated in FIG. 5 may involve disposing active or passive fiduciary markers, respectively, 507, 508, e.g., spherical markers, in relation to at least one of the access port 504 or the external scope 505 for facilitating their tracking (location of these tools) by the tracking system (e.g. tracking system 213 of FIG. 2). The active or passive fiduciary markers, 507, 508, are sensed by sensors of the tracking system 213, whereby identifiable points are provided. A tracked instrument is typically indicated by sensing a grouping of active or passive fiduciary markers, 507, 508, whereby a rigid body, such as a tool, is identified by the tracking system 213, and whereby the position and orientation in 3D of a tracked instrument, such as a tool, is determinable. Namely, a substantially rigid tool can be tracked in 3D space to effectively locate and orient the tool and its various segments and constituent components, provided such segments/components are previously defined and stored against the tracked tool type. Accordingly, a tracked tool may invoke not only general tracking, but also tracking, for example, of the tool's tip or body, and any sensors, as will be detailed below, that may be operatively coupled thereto in a designated configuration (e.g. at or near a tool tip, angled relative to a tool tip or shaft, displaced and/or angled relative to other tool-mounted sensors, etc.). Typically, a minimum of three active or passive fiduciary markers, 507, 508, are placed on a tracked tool to define the instrument. In the several figures included herewith, four active or passive fiduciary markers, 507, 508, are used to track each tool, by example only.

In one particular example, the fiduciary markers comprise reflectosphere markers in combination with an optical tracking system to determine spatial positioning of the surgical instruments within the operating field. The spatial position of automated mechanical arm(s) or robotic arm(s) used during surgery may also be tracked in a similar manner. Differentiation of the types of tools and targets and their corresponding virtual geometrically accurate volumes can be determined by the specific orientation of the reflectospheres relative to one another giving each virtual object an individual identity within the navigation system. The individual identifiers can relay information to the system as to the size and virtual shape of the tool within the system. The identifier can also provide information such as the tool's central point, the tools' central axis, the tool's tip, etc. The virtual tool may also be determinable from a database of tools provided to the navigation system 200. The marker positions can be tracked relative to an object in the operating room such as the patient. Other types of markers that can be used may include, but are not limited to, radio frequency (RF), electromagnetic (EM), pulsed and un-pulsed light-emitting diodes (LED), glass spheres, reflective stickers, unique structures and patterns, wherein the RF and EM would have specific signatures for the specific tools to which they would be attached. The reflective stickers, structures, and patterns, glass spheres, LEDs could all be detected using optical detectors, while RF and EM could be detected using antennas. Advantages to using EM and RF tags may include removal of the line of sight condition during the operation, where using the optical system removes the additional noise from electrical emission and detection systems.

In a further embodiment, printed or 3D design markers can be used for detection by an auxiliary camera and/or external scope. The printed markers can also be used as a calibration pattern to provide distance information (3D) to the optical detector. These identification markers may include designs such as concentric circles with different ring spacing, and/or different types of bar codes. Furthermore, in addition to using markers, the contours of known objects (e.g., side of the port, top ring of the port, shaft of pointer tool, etc.) can be made recognizable by the optical imaging devices through the tracking system 213. Similarly, or in addition thereto, structural information relating to each tool (size, dimensions, distance and geometric orientation relative to markers) may be used to extrapolate the position and orientation various tool segments, such as the tool tip, and various sensors that may be operatively mounted thereon or associated therewith, as noted above.

As will be appreciated by the skilled artisan, while the above lists a number of tracking techniques and related marker types, other known and future techniques may also be considered within the present context to support and enhance operation of the tracked surgical tools, i.e. sensored tools, described herein. Namely, the tracking technique for each instrument will generally allow for the tracking of the instrument's position and orientation within a given frame of reference, in which the position and orientation can be tracked, relayed and/or rendered on the surgical system's one or more displays to visually locate the tool, or data/images acquired thereby, within the context of the procedure taking place and/or any otherwise available pre-operative and/or intraoperative images/details.

Figure 6A:
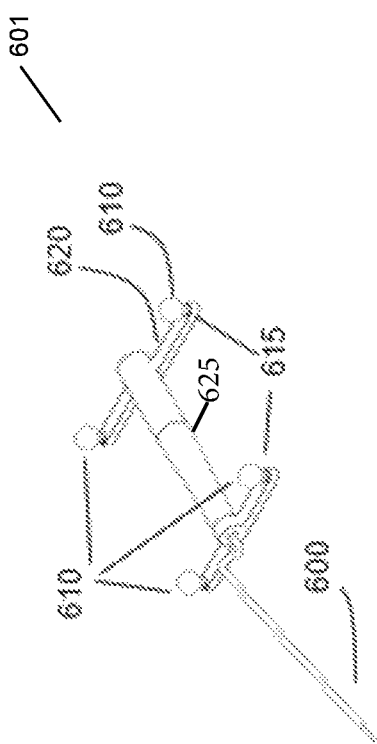
FIGS. 6A to 6D are perspective views of respective trackable pointing tools having distinctly configured tracking markers, in accordance with different embodiments of the present disclosure.

With reference to FIG. 6A, and in accordance with one illustrative embodiment, a perspective view of an exemplary surgical tool 601 is provided, wherein the tool 601 comprises a rigid pointer or pointing tool 600 rigidly coupled to a set of tracking markers 610 fixedly disposed relative thereto in a designated configuration geometry that is recognizable by the tracking system (e.g. tracking system 213 of FIG. 2). In this example, the markers 610 are fixedly coupled to the pointing tool 600 via respective connector beams 615 attached to respective laterally extending arms 620 forming a box-like configuration in a plane of the tool's handle 625.

Figure 6B:
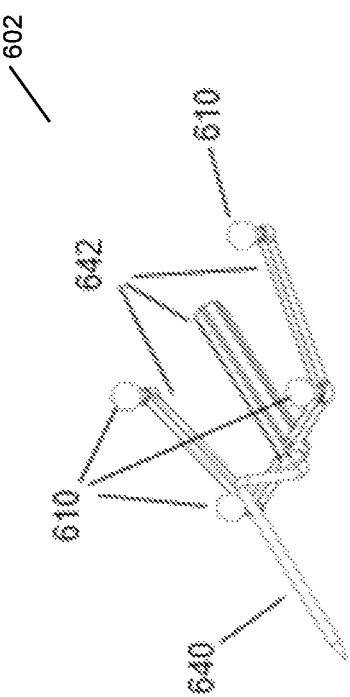

FIG. 6B, provides another example of a tracked surgical tool 602, again defined by a pointer or pointing tool 640 and related tracking markers 610, this time rigidly coupled to the pointing tool 640 via a laterally splayed support arm structure 642.

Figure 6C:
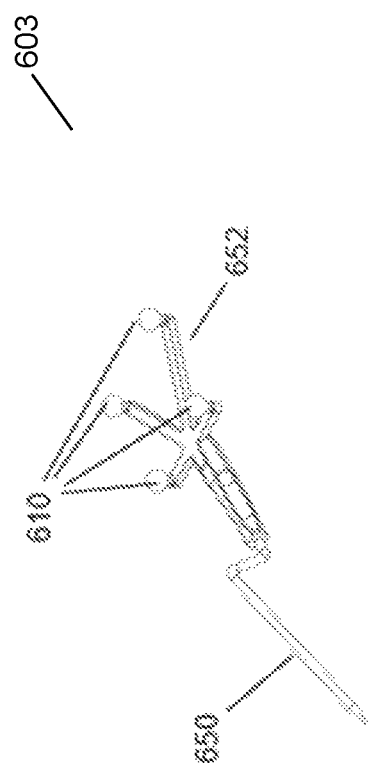

Likewise, FIG. 6C provides another example of a tracked surgical tool 603, again defined by a pointer or pointing tool 650 and related tracking markers 610, this time rigidly coupled to the pointing tool 650 via an intersecting support arm structure 652.

Figure 6D:
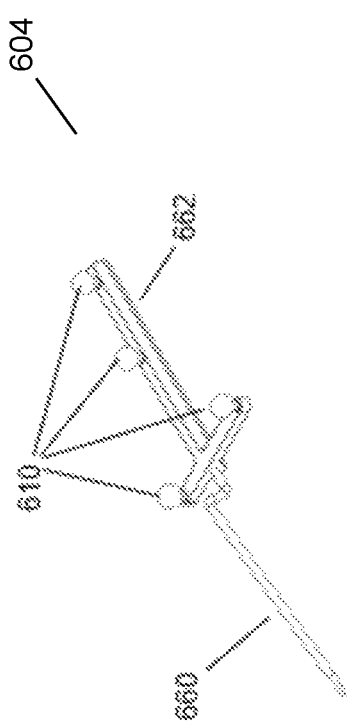
Figure 6F:
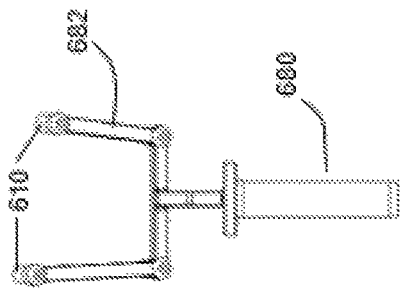
FIGS. 6E to 6H are perspective, front elevation, side and top plan views, respectively, of a trackable surgical access port having a set of tracking markers, in accordance with an embodiment of the present disclosure.
Figure 6H:
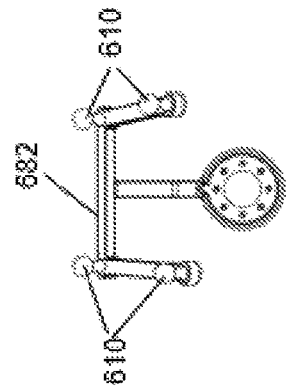
Figure 6E:
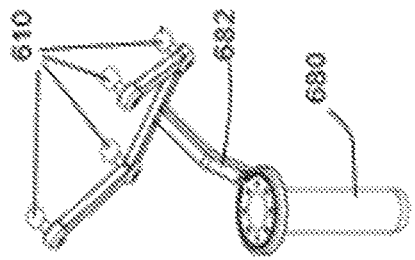
Figure 6G:
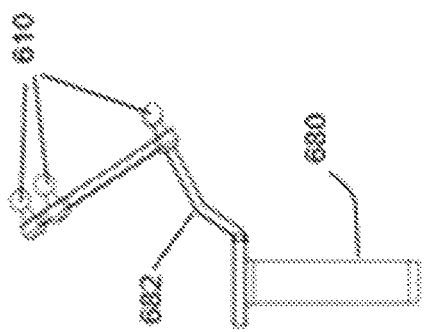

FIG. 6D provides yet another example of a tracked surgical tool 604, again defined by a pointer or pointing tool 660 and related tracking markers 610, this time rigidly coupled to the pointing tool 660 via a T-shaped support arm structure 662.

In each of the examples shown by FIGS. 6A to 6D, the tracked tool includes a pointing tool, though other surgical instruments may also be considered within the present context to provide a like effect. For instance, a suction or resection tool, or other surgical probe, may also be considered in which tracking is effectively provided by appropriate markers and a tracking system, and whereby a position and orientation of the tracked tool may be adequately tracked, relayed and rendered during the procedure. As detailed further below, the further instrumentation of the surgical tool (i.e. sensored tool tip), be it a pointing or other tool, to acquire inner-cavity data and/or images, as considered herein, may also apply to enhance real-time intraoperative data/imaging resources.

For completeness, and with reference to FIGS. 6E to 6H, other surgical devices may also be intraoperatively tracked, as noted above. For example, these figures respectively provide perspective, front elevation, side and top plan views of a surgical port 680 rigidly associated with a corresponding set of markers 610 coupled thereto via a support structure 682. The illustrated arrangement enables clear visibility of the fiducial or tracking markers 610 to the tracking system 213, while ensuring that the markers 610 do not interfere with surgical tools that may be inserted through the access port 680. The non-uniform structure of the extended arm 682 for the markers 610 enables the tracking system 213 to discern both the position and orientation of the access port 680 in response to instructions corresponding to the tracking software, for example.

Figure 7:
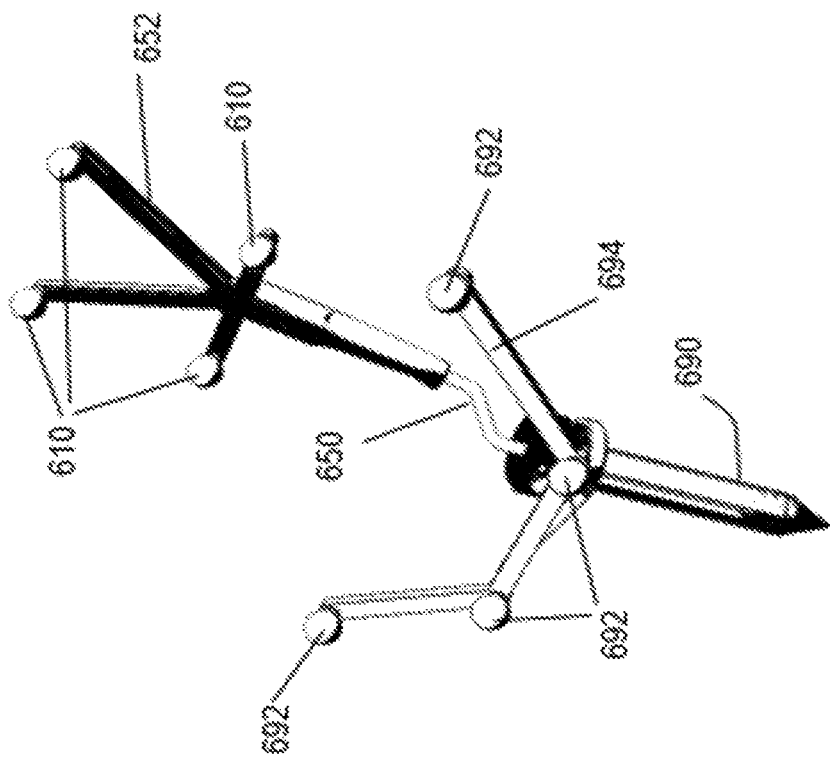
FIG. 7 is a perspective view of the pointing tool of FIG. 6C, engaged with a trackable access port, in accordance with an embodiment of the present disclosure.

With reference to FIG. 7, and in accordance with one embodiment, the tracked tool 603 of FIG. 6C is shown engaged with a tracked access port 690, whereby the tracking markers 610 rigidly associated with the pointing tool 650 via support structure 652 are automatically discernable by the tracking/navigation system from the tracking markers 692 rigidly associated with the access port 690 via distinct support structure 694. Accordingly, the pointing tool 650 and access port 690 are separately trackable by the tracking system 213 of the navigation system 200 and are differentiable as unique objects in images rendered on the display device 205.

As noted above, by mapping each instrument's position and orientation, the tracking system (e.g. system 213 of FIG. 2) may also generally extrapolate a location and orientation of the instrument's various segments, such as an instrument's tip for example, when located and used within the surgical cavity (i.e. down-port location and orientation in the context of a port based procedure). Accordingly, by instrumenting the tip or other segment of a trackable tool, instrumentation-related (sensor) data may also be dynamically associated with the tracked position and orientation of the tool (i.e. tool tip), and effectively mapped in relation thereto even when the tool tip location is obscured to the external viewer/scope. Therefore, a tracked sensored tool, e.g. tool tip, may provide real-time intraoperative visibility otherwise unavailable using pre-operative imaging and intraoperative external scope or camera view angles. Using video and image overlays, as introduced above, tracked tool tip instrumentation may further accentuate available intraoperative data by enhancing real-time data available during the procedure, which is otherwise unavailable using an external scope and cameras.

For example, a tracked sensored tool tip may be enhanced via the disposition of one or more cameras (e.g. miniature camera with a micro lens) at the tool tip to provide real-time intraoperative inner-cavity or down-port (within the context of a port-based procedure) images. For example, such down-port or inner-cavity real-time visible intraoperative imaging may allow for the real-time capture of otherwise obscured or challenging inner-cavity views.

Alternatively, or in combination therewith, the tracked tool tip may be sensored with one or more sensors (e.g. micro-sensors) such as a pressure sensor or the like to capture distinct or further inner-cavity or down-port characterizations otherwise unavailable. For example, a tracked displaceable down-port or inner-cavity pressure sensor may allow for the effective location of an obscured bleeding site, for example, which can then be more effectively addressed (e.g. via bipolar or other method) as compared to current methods, which generally require a blind or mostly obscured visual extra-cavity assessment. These examples will be expanded on further below, with reference to specific embodiments.

With reference to FIG. 3, and in accordance with one embodiment, a sensored surgical tool, generally referred to using the numeral 1500, will now be described. In this embodiment, the tool 1500 generally comprises a rigid elongate tool body 1502 having a substantially rigid tool tip 1504, in this embodiment the tip 1504 forming part of a detachable/disposable sensored tool tip portion 1506 operatively coupled partway up the tool body 1502, i.e. to a tool shaft or rod 1503. The tool shaft 1503 integrally leads to a tool body handle 1508 and tracking portion, such as tracking marker tree 1510 encompassing a set of configurationally and recognizably predisposed tracking markers 1512 (i.e. fiducial markers), such as those previously discussed with respect to the examples of FIGS. 6A to 6D.

For instance, the tool's tracking marker tree 1510 may include a set of tracking markers 1512 rigidly mounted in a distinctly recognizable geometric configuration via a designated support structure (e.g. an instrument-specific marker configuration and/or type for automated tool type recognition and comprehensive real-time tracking/display). The various tracking techniques, marker types and configurations described above are equally applicable in this example.

The tool's body handle 1508 may be configured and adapted for its intended use, be it for manual operation or again for guided or automated operation by a robotic arm or the like, that is, amenable for operative coupling to a robotic arm coupler, grip or clasp, as the case may be. In this particular example, the body handle 1508 and tracking portion 1510 are shaped and oriented relative to the tool body shaft 1503 and tip portion 1506 so to remain visible to the tracking system (i.e. optical tracking system 213 of FIG. 2) and related overhead camera(s), while limiting a potential obstruction thereof to the external scope and/or cameras (e.g. so not to overly obstruct a surgeon's external overhead view angles. These and other tracking portion configurations, as illustrated for example in FIGS. 6A-6D, may be considered, as will be readily appreciated by the skilled artisan.

With added reference to FIGS. 4A and 4B, the detachable/disposable tip portion 1506 comprises one or more tool tip sensors, in this embodiment consisting of one or more imaging sensors such as cameras 1516 and/or one or more pressure sensors 1518 or like pressure-sensitive transducers, for example. Each camera and/or sensor is operatively mounted at or near the tip 1504 to capture inner-cavity images and/or measurements, respectively, which can be relayed in real-time, in this embodiment, via respective embedded wiring 1520 and corresponding contacts 1521 (e.g. quick connect contact points) operatively disposed on the detachable tip portion 1506 to cooperate with corresponding contacts (not shown) and wiring on the reusable tool body shaft 1503 (FIG. 3). Different types of contacts 1521 may be considered, such as pressure-fitting or magnetized contacts, or again touch contact spots solidly connected via a cooperative engagement or coupling linking the removable tip portion 1506 and tool body shaft 1503 (e.g. snap coupling, pressure-fitted coupling, mating engagement fitting, etc.). These and other contact and component coupling techniques may be readily applied within the context of the illustrated embodiment without departing from the general scope and nature of the present disclosure. Likewise, while distinct "four-channel" contacts are illustrated to communicatively link the various tool tip sensors to the RF transmitter via respective wiring, different signaling configurations may also be considered, such as joint cabling and connector configurations, and multiplexing data channeling configurations relying, at least in part, on tip-based data preprocessing and communication hardware, to name one example.

While not explicitly illustrated herein, appropriate power can also be delivered to the sensors, as appropriate, to operate same. Likewise, an appropriate illumination source, such as a miniature LED light source or the like, may be directly mounted at, near or in relation to the tip, or the illumination thereof relayed thereto via an appropriate waveguide or fiber, as needed, and as will be readily appreciated by the skilled artisan, to provide appropriate illumination for image capture if such illumination is not sufficiently available from external illumination sources.

Referring to FIG. 3, in the illustrated embodiment, the embedded wiring is routed to a wireless communication device, for instance comprising a radio frequency (RF) antenna 1522 and RF circuitry 1524 operable to relay data signals produced by the tip sensor(s) 1516/1518 to a corresponding RF receiver and antenna 1526 associated with a (wireless) input/output (I/O) device & interface 1527 and related communication interface(s) 1528 of the surgical system's control and processing unit 1530, or a subcomponent or module thereof, for example.

For instance, sensor data signals can be processed (i.e. via processor 1532 and memory 1534 of the processing unit 1530) in conjunction with the system's tracking/navigation system 1536 and related image processing and display functions (i.e. schematically depicted as display submodule 1538) in real-time for display alone or in combination with one or more other procedure-related visualizations (e.g. pre-operative and/or intraoperative image overlays, pressure data mappings and/or localizations, etc.). Tool tip inner-cavity imaging and/or pressure characterizations may be externally communicated via the illustrated wiring 1520 and RF communication hardware 1524/1522, or again via other direct or indirect communication means, such as via one or more electrical, optical and/or wireless data relays, and the like, embedded or otherwise operatively coupled to the sensored tool 1500.

With particular reference to FIG. 4A, the detachable tool tip portion 1506 comprises a rigid (i.e. metal or plastic) sheath 1542 within which the sensor wiring 1520 may be embedded or relayed, and which forms the surface of the tip 1504 that interfaces with the patient's inner-cavity (e.g.

down-port) tissues/fluids. Embedded within, on and/or through this sheath 1542 toward the tip 1504, i.e. on or at least partly embedded within or through a laterally, or mostly laterally oriented surface of the sheath tip portion 1506 at or toward the tip 1504, are located the camera(s) 1516 and/or pressure sensor(s) 1518 in operative connection with their respective wiring 1520.

With particular reference to FIG. 4A, and in accordance with one exemplary embodiment, the tip portion 1506 includes two cameras 1516 juxtaposed lengthwise along and toward the tip 1504 such that the camera closest to the tip 1504 is angled (A) longitudinally/downwardly (i.e. toward a cavity bottom in operation) relative to the camera farthest from the tip 1504. This configuration allows, in some examples, for distinct inner cavity intraoperative view angles that can, when processed, provide different down-cavity view points to enhance visibility and a visual explorative imaging capacity of the sensored tool 1500 (FIG. 3), and/or be combined to construct or contribute to the construction of a 3D intraoperative down-cavity image. For example, one of the cameras may be particularly oriented to capture surgical cavity sidewall images, whereas the other seeks to predominantly capture cavity bottom views. In some examples, images captured from respective tip cameras can be stitched together to enlarge a field of view of the cavity sidewall. In different embodiments, the two cameras may be juxtaposed side-by-side, on opposite sides of the tip 1504, or consist of a single tip camera, to name a few examples.

With particular reference to FIG. 4B, the tip portion 1506 further includes at least one, and in this case two pressure sensors 1518, one disposed on either side of the longitudinally disposed cameras 1516. Again, distinct pressure readings may be used to provide distinctly localized pressure readings, combined to provide an average reading corresponding to a general location of the tip 1504, or used and/or processed in different combinations, such as to compute real-time localized pressure gradients and/or variations, to name a few examples. A pressure sensor array may also be used to further enhance pressure reading versatility. As for the images relayed from the cameras 1516, pressure readings may also be used to pinpoint localized pressure readings of interest (e.g. anomalously high pressure readings, such as corresponding to a bleeding site or the like, sharp pressure gradients leading to anomalous down-cavity issues, again such as a bleeding site, etc.), or again generate a localized down-cavity pressure mapping, with such results ultimately displayable alone or in concert with other pre-operative and/or intraoperative images, readings and/or measurements. Again, while two pressure sensors 1518 are shown in this embodiment, a single pressure sensor or a plurality of pressure sensors in varying configurations may be used to enhance pressure readings and sensory data complexity. For example, in one embodiment, a pressure sensor array can be used to more accurately map pressure variations within the cavity and thus more readily pinpoint a bleeding site (e.g. from a vein or artery hole), for example, or other anomalous pressure point.

Various cameras may be amenable for use within the present context provided they have a sufficiently small footprint to accommodate the size and area available at the tool tip 1504. For example, a complementary metal oxide semiconductor (CMOS) camera with an integrated micro lens may be particularly amenable for use in the present context to generate high-resolution inner cavity images. For example, the minimal form factor image sensor NanEye 2D by Awaiba™ (http://www.cmosis.com/products/product_detail/naneye) provides one example of a system on a chip camera having a footprint of approximately $1 \times 1$ mm$^2$. For a tool tip portion diameter in the range of 4 to 5 mm, a camera footprint of this order may be suitable, even when combining two cameras and two pressure sensors in the same tip area. Clearly, where a single camera is used, a larger footprint, for example in the range of $2 \times 2$ mm$^2$ or higher may also be suitable.

Furthermore, each of the one or more cameras may consist of self-contained camera units, thus comprising any and all circuitry to implement the camera and capture images (e.g. pixelated/digital images) therewith, as well as any necessary optics (e.g. micro lens) integrally formed therewith. In other embodiments, additional components, such as external lenses or the like, may be provided, for example within the sheath illustrated herein, or again, as an add-on component, to provide a desired imaging effect. Generally, the camera(s) will be sealed in a waterproof configuration to ensure proper operation within the surgical environment and reduce the likelihood of camera failures. Likewise, while identical though distinctly oriented cameras are shown in the illustrated embodiments, different camera characteristics may be considered to provide complementary effects (e.g. narrow vs. wide angle lens, different image spectrum sensitivity such as narrow band vs. broadband and/or visible vs. near infrared cameras, etc.). Furthermore, while not explicitly illustrated in the embodiments of FIGS. 3, 4A and 4B, the sensored tip may further include, as noted above, an integrated illumination device, such as a miniature LED light source or the like to provide required or complementary (i.e. complementary to external illumination) innercavity illumination for effective image capture. In yet another example, the tool may further include a directional light source such as a laser light source to gauge a distance to the imaged or characterized tissue by measuring reflected laser light travel times, for example.

Likewise, different pressure sensor technologies may be invoked to provide an appropriate tool tip sensor. For example, different fabry-perot, piezoresistive, nanotube and/or optical microelectromechanical (MEMS) pressure sensors may be amenable to the herein-described application. Examples of such sensors are respectively described by G. C. Hill, et al. 2007, SU-8 MEMS Fabry-perot pressure sensor, *Sensors and actuators A* 138(2007) 52-62; Jialin Yao, et al., 2016, A flexible and highly sensitive piezoresistive pressure sensor based on micropatterned films coated with carbon nanotubes, *Journal of Nanomaterials, Volume 2016*; and Yixian Ge, et al., An optical MEMS pressure sensor based on a phase demodulation method, *Sensors and actuators A* 143(2008) 224-229; the entire contents of each of which are hereby incorporated herein by reference. Other pressure sensor types may also be considered, without departing from the general scope and nature of the present disclosure.

As noted above, other surgical tools may be effectively sensored and tracked by the surgical system's tracking hardware to provide enhanced inner cavity characterization and/or imaging. For example, a suction tool may be commonly used when the surgical cavity is immersed in blood or fluid in order to seek out a bleeding or leaking site to be addressed. Accordingly, such suction tool may be advantageously fitted with one or more cameras and/or pressure sensors, as noted above, to improve inner cavity assessment while using the tracked suction tool. Much like the pointing tool described above with reference to FIGS. 3, 4A and 4B, the suction tool may encompass a sensored tip, i.e. laterally oriented sensors operatively mounted on an axially or opposing laterally directed suction tool. Alternatively, the suction tool may be combined with a distinct pointing tool portion, much as described above, to provide dual functions. Such as described above, a suction tool tip portion may consist of a disposable tip portion that may be replaced for each new procedure. As will be appreciated by the skilled artisan, other surgical tools may equally benefit from sensor borne tool tips as described above, not only to improved inner cavity imaging/characterization intraoperatively, but also to accelerate certain surgical site processes by accurately imaging, locating and mapping inner cavity characteristics to be addressed or considered in real-time during the surgical procedure.

With reference back to FIG. 3, the illustrative control and processing unit 1530, which may consist of a standalone or subcomponent of an overall surgical system processing and control unit, may include, but is not limited to comprising one or more processors 1532 (for example, a CPU/microprocessor or a graphical processing unit, or a combination of a central processing unit or graphical processing unit), bus 1544, memory 1534, which may include random access memory (RAM) and/or read only memory (ROM), one or more internal storage devices 1546 (e.g. a hard disk drive, compact disk drive or internal flash memory), a power supply 1548, one more communications interfaces 1528, optional external storage 1550, display image/data processing 1538, and one or more input/output devices and/or interfaces 1527 (e.g., a wireless receiver/transmitter and antenna 1526, a speaker, a display (i.e. one or more displays 205, 211 of FIG. 2 and/or a linked graphical user interface (GUI) or the like), an imaging sensor, such as those used in a digital still camera or digital video camera, a clock, an output port, a user input device, such as a keyboard, a keypad, a mouse, a position tracked stylus, a foot switch, and/or a microphone for capturing speech commands).

Control and processing unit 1530 may be programmed with programs, subroutines, applications or modules, which include executable instructions, which when executed by the processor, causes the system to perform one or more methods described in the disclosure. Such instructions may be stored, for example, in memory 1534 and/or internal storage 1546. In particular, in the exemplary embodiment shown, image processing module 1538 includes computer executable instructions for analyzing output tool tip sensor data (images and/or pressure readings). For example, computer readable instructions may be provided for processing image and/or pressure data obtained at different inner-cavity spatial locations and tool tip orientations in order to image/characterize otherwise potentially obscured regions of the surgical cavity. The spatial location/orientation may be correlated with the recorded image/pressure data via the tracking of the position and orientation of tool 1500, for instance tracked via illustrated tracking and navigation module 1536. For example, the tracking and navigation module 1536 may include executable instructions for processing tracking data, and/or for rendering a navigation user interface on a display, as discussed above.

Although only one of each unit component is illustrated in FIG. 3, any number of each component can be included in the control and processing unit 1530. For example, a computer typically contains a number of different data storage media. Furthermore, although bus 1544 is depicted as a single connection between all of the components, it will be appreciated that the bus 1544 may represent one or more circuits, devices or communication channels which link two or more of the components. For example, in personal computers, bus 1544 often includes or is a motherboard.

Control and processing unit 1530 may include many more or less components than those shown. It is also noted that one or more external subsystems, such as a tool tip sensor data processing device, may be distinctly implemented and communicatively linked to an overall surgical system control and processing unit, or form an integral part thereof.

In one embodiment, control and processing unit 1530 may be, or include, a general purpose computer or any other hardware equivalents. Control and processing unit 1530 may also be implemented as one or more physical devices that are coupled to processor 1532 through one of more communications channels or interfaces. For example, control and processing unit 1530 can be implemented using application specific integrated circuits (ASICs). Alternatively, control and processing unit 1530 can be implemented as a combination of hardware and software, where the software is loaded into the processor from the memory or over a network connection.

Figure 8:
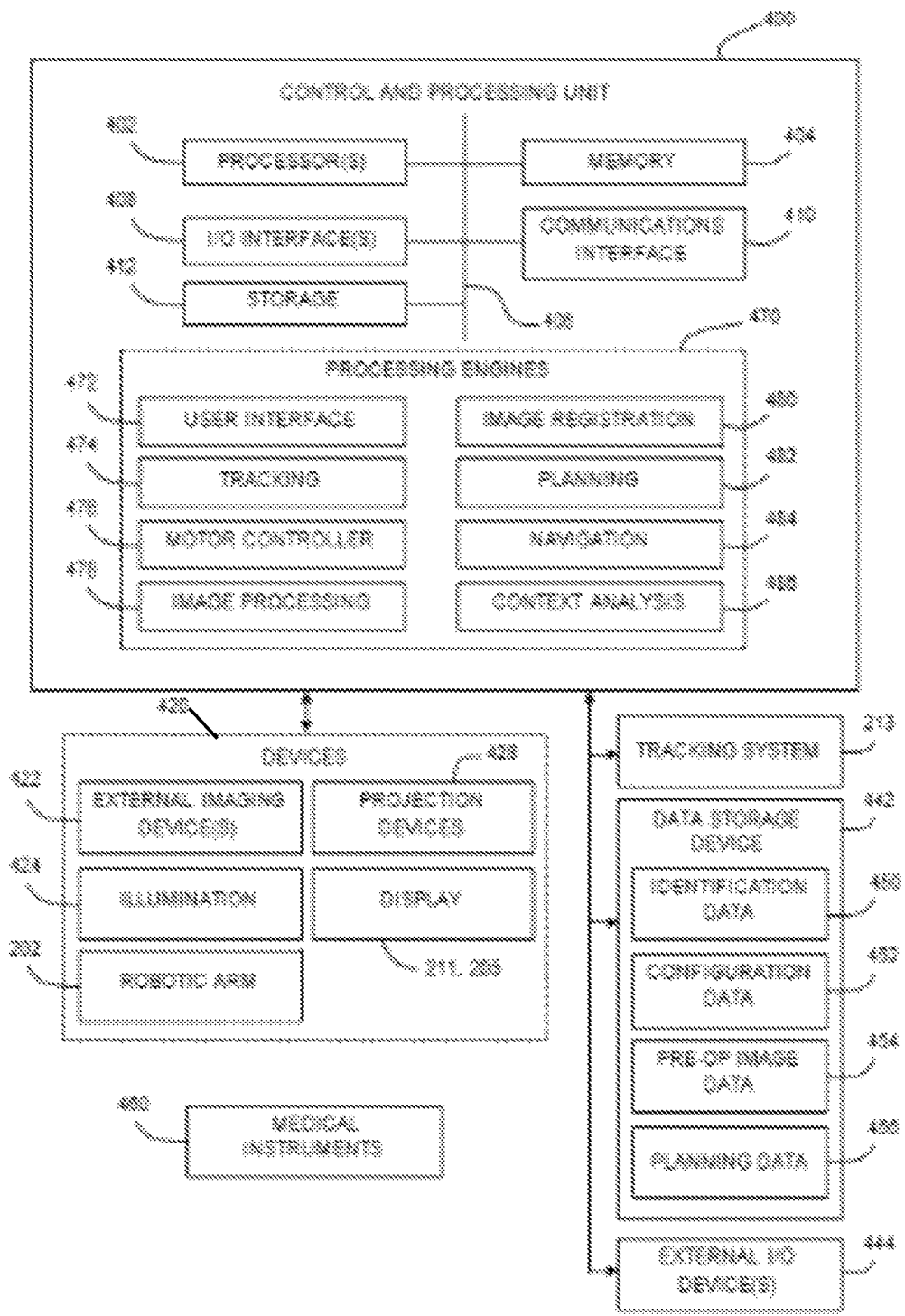
FIG. 8 is a schematic diagram illustrating the relationship between components of a surgical navigation system, such as a control and processing unit, a tracking system, a data storage device for the tracking system, system devices, and medical instruments/tools, in accordance with an embodiment of the present disclosure.

With reference to FIG. 8, and in accordance with one embodiment, relationships between components of an overall surgical navigation system 200, such as a control and processing unit 400, a tracking system 213, a data storage device 442 for the tracking system 213, and system devices 420, and medical instruments 460, will now be described. The control and processing unit 400 comprises at least one processor 402, a memory 404, such as a non-transitory memory device, a system bus 406, at least one input/output interface 408, a communications interface 410, and storage device 412. The control and processing unit 400, which may encompass or interface with control and processing unit 1530 of FIG. 3, is interfaced with other external devices, such as the tracking system 213, data storage 442 for the tracking system 213, and external user input and output devices 444, optionally comprising, for example, at least one of a display device, such as display devices 211, 205, a keyboard, a mouse, a foot pedal, a microphone, and a speaker.

The data storage 442 comprises any suitable data storage device, such as a local or remote computing device, e.g. a computer, hard drive, digital media device, or server, having a database stored thereon. The data storage device 442 includes identification data 450 for identifying at least one medical instrument 460 and configuration data 452 for associating customized configuration parameters with at least one medical instrument 460. The data storage device 442 further comprises at least one of preoperative image data 454 and medical procedure planning data 456. Although data storage device 442 is shown as a single device, understood is that, in other embodiments, the data storage device 442 comprises multiple storage devices. The data storage device 442 is also configured to store data in a custom data structure corresponding to various 3D volumes at different resolutions, wherein each may be captured with a unique time-stamp and/or quality metric. This custom data structure provides the system 200 (FIGS. 1 and 2) with an ability to move through contrast, scale, and time during the surgical procedure.

Medical instruments (tools) 460 are identifiable by the control and processing unit 400, wherein the medical instruments 460 are coupled with, and controlled by, the control and processing unit 400. Alternatively, the medical instruments 460 are operable or otherwise independently employable without the control and processing unit 400. The tracking system 213 may be employed to track at least one of the medical instruments 460 and spatially register the at least one medical instrument 460 in relation to an intraoperative reference frame. As noted above, the tracking system 213 may thus furnish the requisite position, orientation and location data to associate sensed tool data with corresponding locations within the surgical cavity.

The control and processing unit 400 is also interfaceable with a number of configurable devices, and may intra-operatively reconfigure at least one such device based on configuration parameters obtained from configuration data 452. Examples of devices 420 include, but are not limited to, at least one external imaging device 422, at least one illumination device 424, robotic arm 202, at least one projection device 428, and at least one display device, such as display devices 211, 205.

The control and processing unit 400 is operable by the at least one processor 402 and the at least one memory 404. For example, the functionalities described herein are at least partially implemented via hardware logic in processor 402 by way of the instructions stored in memory 404 though at least one processing engine 470. Examples of processing engines 470 include, but are not limited to, user interface engine 472, tracking engine 474, motor controller 476, image processing engine 478, image registration engine 480, procedure planning engine 482, navigation engine 484, and context analysis module 486. Understood is that the system 200 (FIGS. 1 and 2) is not intended to be limited to the components shown in the several figures of the Drawing. One or more components of the control and processing 400 may be provided as an external component or device. In one alternative embodiment, navigation module 484 may be provided as an external navigation system that is integrated with control and processing unit 400.

Embodiments of the system 200 of FIG. 2 may be implemented using processor 402 without additional instructions stored in memory 404. Embodiments may also be implemented using the instructions stored in the memory 404 for execution by one or more general purpose microprocessors.

Thus, the disclosure is not limited to a specific configuration of hardware, firmware, and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The preceding exemplary embodiments involve systems and methods in which a device is intra-operatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids (e.g. wash fluids) during the medical procedure, and may further identify the type of fluid. Each of these examples relate to the image-based identification of information pertaining to the context of the medical procedure.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Figure 9:
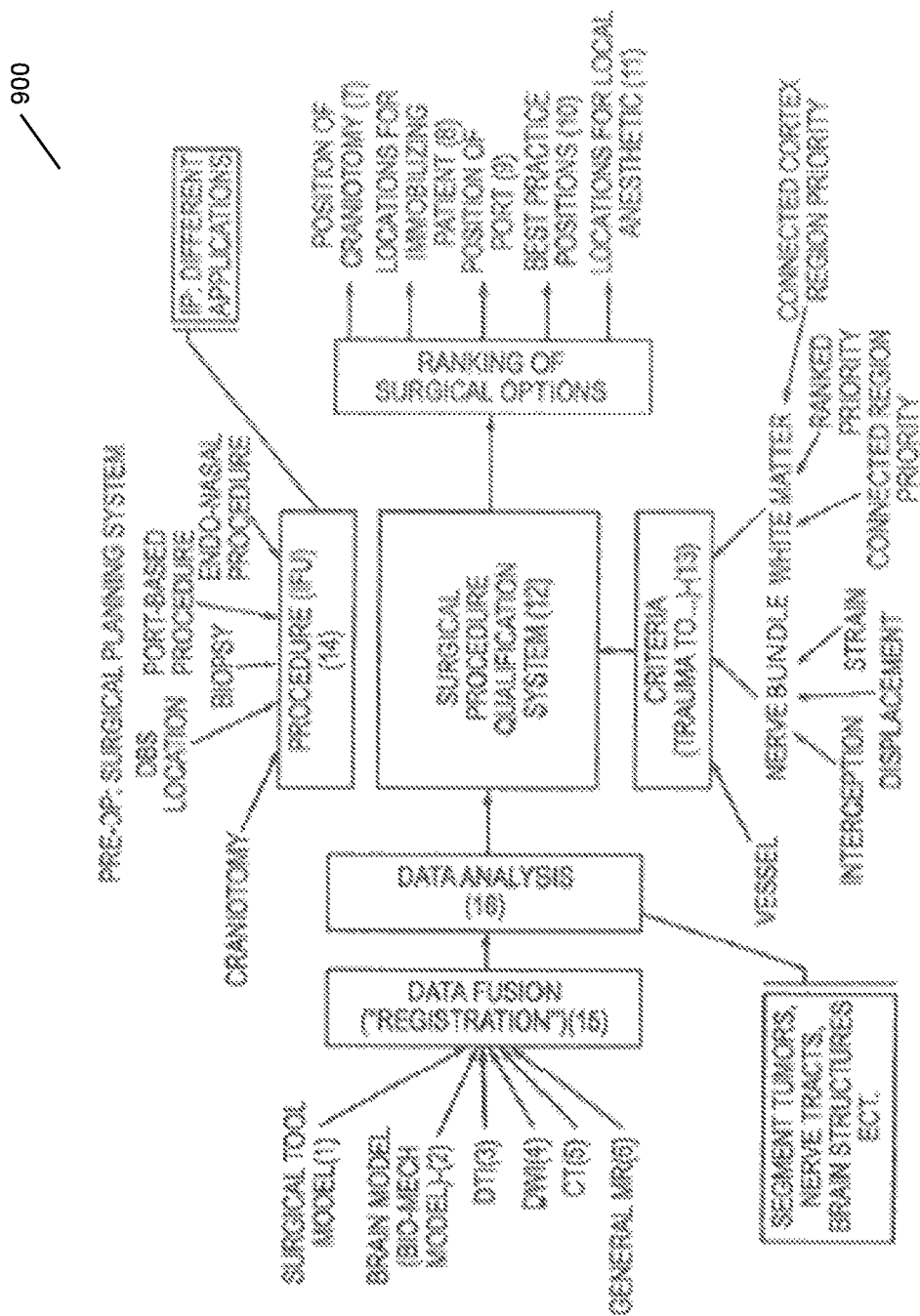
FIG. 9 is a schematic diagram illustrating a pre-operative surgical planning system for use with a medical navigation system, in accordance with an embodiment of the present disclosure.

With reference to FIG. 9, a schematic diagram is provided to illustrate a pre-operative surgical planning system 900 for use with a navigation system 200, in accordance with an embodiment of the present disclosure. The pre-operative surgical planning system 900 comprises components and inputs for planning and scoring surgical paths.

Figure 10:
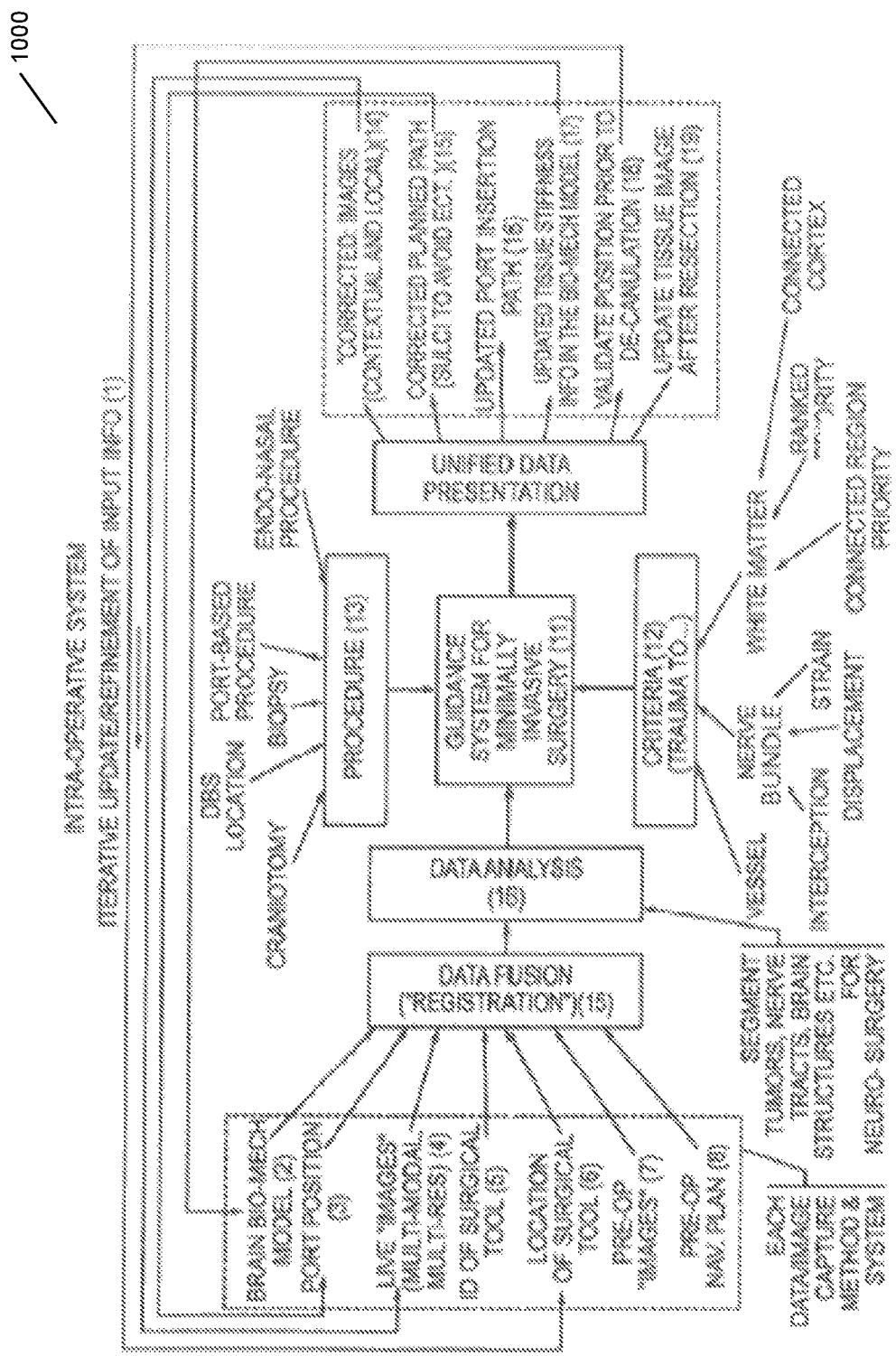
FIG. 10 is a schematic diagram illustrating an intraoperative surgical management system for use with a medical navigation system, in accordance with an embodiment of the present disclosure.

With reference to FIG. 10, a schematic diagram is provided to illustrate an intraoperative surgical management system 1000 for use with a navigation system 200, in accordance with an embodiment of the present disclosure. The intraoperative surgical management system 1000 comprises components and inputs for navigation along the surgical paths produced by the pre-operative surgical planning system 900, as shown in FIG. 9. The intra-operative surgical management system 1000 can be used as a surgical planning and navigation tool in the pre-operative and intra-operative stages. Data input(s) of the surgical planning steps and surgical procedures, as shown in FIG. 9, can be used as input(s) to the intra-operative navigation stage performable by the intra-operative surgical management system 1000.

The intra-operative surgical management system 1000 of the navigation system 200 provides a user, such as a surgeon, with a unified technique for navigating through a surgical region by utilizing pre-operative data input(s) and updated intra-operative data input(s). The processor(s), such as the at least one processor 402, is operable by way of a set of instructions and/or algorithms storable in relation to a non-transitory memory device, such as the at least one memory 404, wherein the at least one processor 402 is configured to: analyze pre-operative data input(s) and intra-operative data input(s) and update surgical plans during the course of surgery accordingly.

For example, if intra-operative input(s) in the form of newly acquired images identified a previously unknown or unidentified nerve bundle or a previously unknown or unidentified fiber track, the at least one processor 402 can use these intra-operative input(s), if desired, for updating the surgical plan during surgery to avoid contacting the nerve bundle. The intra-operative input(s) may include a variety of input(s), including local data gathered using a variety of sensor(s), such as at least one intra-operative imaging sensor (not shown). In some embodiments, the intra-operative surgical management system 1000 of the navigation system 200 may provide continuously updated, e.g., in real-time, intra-operative input(s) in the context of a specific surgical procedure by way of the at least one intra-operative imaging sensor to: validate tissue position, update tissue imaging after tumor resection, and update surgical device position during surgery.

Still referring to FIG. 10, the intra-operative surgical management system 1000 of the navigation system 200 may provide for re-formatting of the image, for example, to warn of possible puncture of, or collision with, critical tissue structures with a surgical tool during surgery. In addition, the intra-operative surgical management system 1000 may provide imaging and input updates for any shifts or surgical errors that might occur from a needle deflection, tissue deflection, or patient movement as well as provide analysis and transformation of data to correct for imaging distortions, e.g., in real-time. The magnitude of these combined shifts or surgical errors is clinically significant and may regularly exceed 2 cm. Some of the most significant distortions are magnetic resonance imaging (MRI) based distortions such as gradient non-linearity, susceptibility shifts, and eddy current artifacts, which may exceed 1 cm on standard MRI scanners (1.5 T and 3.0 T systems). The intra-operative surgical management system 1000 mitigates, and may eliminate, these combined shifts or surgical errors.

In accordance with some embodiments of the present disclosure, by using the a intra-operative surgical management system 1000, a variety of intra-operative imaging techniques may be implemented to generate intra-operative input(s) by way of a variety of imaging devices, including anatomy specific MRI devices, surface array MRI scans, endo-nasal MRI devices, anatomy specific ultrasound (US) scans, endo-nasal US scans, anatomy specific computerized tomography (CT) or positron emission tomography (PET) scans, port-based or probe based photo-acoustic imaging, sensored tool imaging and/or characterization, as well as optical imaging done with remote scanning, or probe based scanning, whereby multi-modal imaging and data are providable and transformable into useful images and data in real-time.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A surgical tool for use within an open surgical cavity, the surgical tool comprising:

a rigid elongate tool body having a substantially rigid tool tip to be displaced and tracked within the open surgical cavity to reproducibly locate said substantially rigid tool tip within the open surgical cavity;

a pressure sensor operatively disposed along said rigid elongate tool body at a position, in one of at the substantially rigid tool tip and proximate said substantially rigid tool tip, the pressure sensor responsive to pressure variations applied thereto from within the open surgical cavity to output a sensor signal representative thereof as the substantially rigid tool tip is displaced within the open surgical cavity, said sensor signal externally communicable to associate respective inner-cavity pressure readings with locations of the substantially rigid tool tip, and the pressure sensor comprising at least one of: a Fabry-Perot pressure sensor, a piezoresistive pressure sensor, nanotube pressure sensor, and an optical microelectromechanical (MEMS) pressure sensor;

at least one camera disposed, and laterally-oriented, along said rigid elongate tool body in one of at the substantially rigid tool tip and proximate said substantially rigid tool tip to capture lateral images from within the open surgical cavity, said lateral images externally communicable to further associate respective inner-cavity images with said locations of the substantially rigid tool tip, and the at least one camera operable in a near-infrared wavelength range;

a suction tool configured to operate with another pressure sensor and another at least one camera, the suction tool comprising a suction tool tip portion, the suction tool tip portion comprising a disposable tip portion, wherein imaging, locating, and mapping inner cavity characteristics are considered by an external data processing unit in real-time during a surgical procedure; and the external data processing unit operable to associate a given pressure reading associated with the sensor signal with a corresponding location of the pressure sensor and with a sensor signal from the other pressure sensor within the open externally accessible surgical cavity, said external data processing unit further operable to associate respective inner-cavity images with locations of the substantially rigid tool tip and the location of the suction tool tip portion.

2. The surgical tool of claim 1, wherein said pressure sensor is laterally oriented relative to said substantially rigid tool tip.

3. The surgical tool of claim 2, wherein said pressure sensor comprises a plurality of pressure sensors disposed at a position in one of: at the substantially rigid tool tip and proximate said substantially rigid tool tip.

4. The surgical tool of claim 1, further comprising: a set of fiducial markers externally coupled in a fixed configuration to an externally extending portion of said rigid elongate tool body, wherein said markers are trackable by an external tracking system to automatically determine said locations of the substantially rigid tool tip, with reference to the open surgical cavity, based on a respective tracked position of said markers.

5. The surgical tool of claim 1, further comprising a radio frequency transmitter to wirelessly communicate said sensor signal.

6. The surgical tool of claim 1, wherein said pressure sensor comprises a plurality of pressure sensors collocated at a position in one of: at the substantially rigid tool tip and toward said substantially rigid tool tip.

7. The surgical tool of claim 1, wherein the suction tool is disposed at a position, in one of: at the substantially rigid tool tip and proximate said substantially rigid tool tip, to concurrently provide suction within the surgical cavity around said substantially rigid tool tip.

8. The surgical tool of claim 1,
wherein an external camera is configured to align with, and view, the open surgical cavity, and
wherein said substantially rigid tool tip is operable as a trackable pointer within the open surgical cavity.

9. The surgical tool of claim 1, further comprising at least one complementary camera disposed along said rigid elongate tool body at a position, in one of at the substantially rigid tool tip and proximate said substantially rigid tool tip, to capture complementary images of the open surgical cavity along a complementary imaging axis angled toward a cavity bottom relative to said laterally-oriented camera to construct one of a 3D inner-cavity mapping and an enlarged field of view image of the open surgical cavity from said lateral images and said complementary images.

10. The surgical tool of claim 9,
wherein at least one of an external camera and a scope is configured to align with, and view, the open surgical cavity, and
wherein said inner-cavity images are complementary to external images captured by at least one of the external camera and the scope in enhancing inner-cavity visualization.

11. The surgical tool of claim 1, wherein said substantially rigid tool tip is movable within the open surgical cavity to track pressure variations resulting from inner-cavity bleeding in locating a bleeding site within the open surgical cavity.

12. The surgical tool of claim 1,
wherein said rigid elongate tool body comprises a reusable tool shaft portion and a disposable tool tip portion removably operatively connectable to said shaft portion, and
wherein said disposable tool tip portion comprises said substantially rigid tool tip and said pressure sensor.

13. A surgical system for performing surgery through an open externally accessible surgical cavity, the system comprising:

a surgical tool, the surgical tool comprising: a rigid elongate tool body having a substantially rigid tool tip to be displaced and tracked within the open externally accessible surgical cavity to reproducibly locate said substantially rigid tool tip within the open externally accessible surgical cavity;

a pressure sensor operatively disposed along said rigid elongate tool body at a position, in one of at the substantially rigid tool tip and proximate said substantially rigid tool tip, the pressure sensor responsive to pressure variations applied thereto from within the open externally accessible surgical cavity to output a sensor signal representative thereof as the substantially rigid tool tip is displaced within the open externally accessible cavity, and the pressure sensor comprising at least one of: a Fabry-Perot pressure sensor, a piezoresistive pressure sensor, nanotube pressure sensor, and an optical microelectromechanical (MEMS) pressure sensor;

at least one camera disposed, and laterally-oriented, along said rigid elongate tool body in one of at the substantially rigid tool tip and proximate said substantially rigid tool tip to capture lateral images from within the open externally accessible surgical cavity, the at least one camera operable in a near-infrared wavelength range;

a suction tool configured to operate with another pressure sensor and another at least one camera, the suction tool comprising a suction tool tip portion, the suction tool tip portion comprising a disposable tip portion, wherein imaging, locating, and mapping inner cavity characteristics are considered by an external data processing unit in real-time during a surgical procedure;

an external tracking system operatively interfacing with said surgical tool and the suction tool to automatically track a location of said substantially rigid tool tip and a location of the suction tool tip portion within the open externally accessible surgical cavity; and the external data processing unit operable to associate a given pressure reading associated with said sensor signal with a corresponding location of said pressure sensor and with a sensor signal from the other pressure sensor within the open externally accessible surgical cavity, said external data processing unit further operable to associate respective inner-cavity images with locations of the substantially rigid tool tip and the location of the suction tool tip portion.

14. The surgical system of claim 13,
wherein said surgical tool further comprises a set of fiducial markers externally coupled, in a fixed configuration, with an externally extending portion of said rigid elongate tool body, and
wherein said markers are trackable by an external surgical navigation system to automatically associate said corresponding location of said pressure sensor within the open externally accessible surgical cavity based on a respectively tracked position of said markers.

15. The surgical system of claim 13, wherein said pressure sensor is laterally oriented relative to said substantially rigid tool tip.

16. A surgical tool for use within an open externally visible surgical cavity that is visibly accessible to one of an external camera and a scope aligned therewith, the surgical tool comprising:
   a rigid elongate tool body having a substantially rigid tool tip to be displaced and tracked within the open externally visible surgical cavity so as to reproducibly locate said substantially rigid tool tip within the open externally visible surgical cavity;
   at least one laterally-oriented camera operatively disposed along said rigid elongate tool body at a position, in one of at the substantially rigid tool tip and proximate said substantially rigid tool tip, to capture lateral inner-cavity images of the open externally visible surgical cavity for output as the substantially rigid tool tip is displaced within the open externally visible surgical cavity, said lateral inner-cavity images externally communicable to associate respective lateral inner-cavity images with locations of the substantially rigid tool tip, said inner-cavity images complementary to external images captured by one of said external camera and the scope in enhancing inner-cavity visualization, and the at least one laterally-oriented camera operable in a near-infrared wavelength range; and
   a suction tool configured to operate with a pressure sensor, another pressure sensor, at least one camera, and another at least one camera, the suction tool comprising a suction tool tip portion, the suction tool tip portion comprising a disposable tip portion, wherein imaging, locating, and mapping inner cavity characteristics are considered by an external data processing unit in real-time during a surgical procedure, and the pressure sensor comprising at least one of: a Fabry-Perot pressure sensor, a piezoresistive pressure sensor, nanotube pressure sensor, and an optical microelectromechanical (MEMS) pressure sensor; and
   the external data processing unit operable to associate a given pressure reading associated with said sensor signal with a corresponding location of said pressure sensor and with a sensor signal from the other pressure sensor within the open externally accessible surgical cavity, said external data processing unit further operable to associate respective inner-cavity images with locations of the substantially rigid tool tip and the location of the suction tool tip portion.

17. The surgical tool of claim 16, further comprising a set of fiducial markers externally coupled, in a fixed configuration, with an externally extending portion of said rigid elongate tool body, wherein said set of fiducial markers is trackable by an external tracking system to automatically determine locations of the substantially rigid tool tip, with reference to the cavity, based on a respective tracked position of said markers.

18. The surgical tool of claim 16, further comprising a radio frequency transmitter to wirelessly communicate said lateral inner-cavity images.

19. The surgical tool of claim 16, wherein the suction tool is disposed at a position, in one of at the substantially rigid tool tip and proximate said substantially rigid tool tip, to concurrently provide suction within the open externally visible surgical cavity around said substantially rigid tool tip.

20. The surgical tool of claim 16, further comprising at least one complementary camera disposed along said rigid elongate tool body at a position, in one of at the substantially rigid tool tip and proximate said substantially rigid tool tip, to capture complementary images of the open externally visible surgical cavity along a complementary imaging axis angled toward a cavity bottom relative to said laterally-oriented camera to construct one of a 3D inner-cavity mapping and an enlarged field of view image of the open externally visible surgical cavity from said lateral images and said complementary images.

* * * * *